US010806817B2

(12) United States Patent
Sevy

(10) Patent No.: US 10,806,817 B2
(45) Date of Patent: Oct. 20, 2020

(54) ANNULAR SEPARATOR APPARATUS AND METHOD

(71) Applicant: Earl Vaughn Sevy, Cedar City, UT (US)

(72) Inventor: Earl Vaughn Sevy, Cedar City, UT (US)

( * ) Notice: Subject to any disclaimer, the term of this patent is extended or adjusted under 35 U.S.C. 154(b) by 735 days.

(21) Appl. No.: 15/373,035

(22) Filed: Dec. 8, 2016

(65) Prior Publication Data

US 2017/0165392 A1 Jun. 15, 2017

Related U.S. Application Data

(60) Provisional application No. 62/265,820, filed on Dec. 10, 2015.

(51) Int. Cl.

*A61L 9/14* (2006.01)
*B05B 7/00* (2006.01)
*B05B 7/24* (2006.01)

(52) U.S. Cl.

CPC .............. *A61L 9/14* (2013.01); *B05B 7/0012* (2013.01); *B05B 7/2424* (2013.01); *A61L 2202/11* (2013.01)

(58) Field of Classification Search

CPC ...... A61L 9/14; A61L 2202/11; B05B 7/0012; B05B 7/2424

USPC ............... 239/515, 524, 124, 338, 370, 504; 128/200.18

See application file for complete search history.

(56) References Cited

U.S. PATENT DOCUMENTS

| | | | |
|---|---|---|---|
| 904,149 | A | 11/1908 | Rachmann |
| 2,826,454 | A | 3/1958 | Coanda |
| 3,112,074 | A | 11/1963 | Green |
| 3,515,966 | A | 6/1970 | De Valroger et al. |
| 3,641,757 | A | 2/1972 | Rehn |
| 4,235,611 | A | 11/1980 | Brownell |
| 4,243,396 | A | 1/1981 | Cronenberg |
| 4,976,259 | A | 12/1990 | Higson et al. |
| 5,029,759 | A | 7/1991 | Weber |

(Continued)

FOREIGN PATENT DOCUMENTS

| | | | |
|---|---|---|---|
| JP | 2001046920 | | 9/2002 |
| JP | WO 2009/019797 | * | 2/2009 |

OTHER PUBLICATIONS

Tetra Whisper Aquarium Air Pump 300, Aquarium Guys, Oct. 8, 2008 p. 1, http://www.aquariumguys.com/tetraairpump4.html.

(Continued)

*Primary Examiner* — Qingzhang Zhou

(74) *Attorney, Agent, or Firm* — Pate Baird, PLLC

(57) ABSTRACT

An unheated, essential oil diffuser relies on a pressurized air stream to educt oil from a reservoir, followed by separators including separation chambers and an annular channel. The latter is a long channel having an aspect ratio (L/d) of from about 10 to about 120, for length L and thickness d. Thickness d is effective diameter, also known as hydraulic diameter (4 times c.s. area, divided by "wetted" or exposed perimeter), and may be from about 25 to about 100 thousandths of an inch (0.6 to 2.5 mm) across the thin passage, with a target range of from about 55 to 75 mils (0.7 to 1 mm). This geometry provides laminar flow at Reynolds number values less than a few hundred for virtually its complete distance of from under one inch (25 mm) to over three inches (76 mm).

8 Claims, 17 Drawing Sheets

(56) References Cited

U.S. PATENT DOCUMENTS

| | | | | |
|---|---|---|---|---|
| 5,054,477 | A | 10/1991 | Terada et al. | |
| 5,137,432 | A | 8/1992 | Tsai | |
| 5,201,641 | A | 4/1993 | Richer | |
| 5,248,448 | A | 9/1993 | Waldron et al. | |
| 5,309,900 | A | 5/1994 | Knoch et al. | |
| 5,314,529 | A | 5/1994 | Tilton et al. | |
| 5,409,170 | A * | 4/1995 | Burwell | B05B 7/0012 128/200.18 |
| 5,549,247 | A | 8/1996 | Rossman et al. | |
| 5,579,758 | A | 12/1996 | Century | |
| 5,687,710 | A | 11/1997 | Ambrosio et al. | |
| 5,875,774 | A | 3/1999 | Clementi et al. | |
| 5,922,247 | A | 7/1999 | Shoham et al. | |
| 6,029,913 | A | 2/2000 | Stroia et al. | |
| 6,168,392 | B1 | 1/2001 | Takano | |
| 6,217,281 | B1 | 4/2001 | Jeng et al. | |
| 6,236,042 | B1 | 5/2001 | Kato et al. | |
| 6,364,637 | B1 | 4/2002 | Hase et al. | |
| 6,669,176 | B2 | 12/2003 | Rock | |
| D491,259 | S | 6/2004 | Garrison et al. | |
| D491,258 | S | 7/2004 | Sevy | |
| D492,020 | S | 7/2004 | Sevy | |
| D509,893 | S | 9/2005 | Sevy | |
| 6,968,069 | B1 | 11/2005 | Zhao | |
| D520,129 | S | 5/2006 | Sevy | |
| D526,710 | S | 7/2006 | Sevy | |
| 7,407,118 | B2 | 8/2008 | Sevy | |
| 7,712,683 | B2 | 5/2010 | Robert et al. | |
| 7,878,418 | B2 * | 2/2011 | Sevy | A61M 11/06 128/200.18 |
| 7,930,068 | B2 | 4/2011 | Robert et al. | |
| 8,001,963 | B2 * | 8/2011 | Giroux | A61M 15/08 128/200.14 |
| 9,415,130 | B2 * | 8/2016 | Sevy | A61L 2/00 |
| 2008/0283049 | A1 | 11/2008 | Mahoney et al. | |
| 2012/0251296 | A1 * | 10/2012 | Jorgensen | B05B 17/0607 415/116 |
| 2013/0327323 | A1 | 12/2013 | Rubin | |

OTHER PUBLICATIONS

Optima Air Pump A807, Aquarium Guys, Oct. 8, 2008, p. 1, http://www.aguariumguys.com/optimaairpump.html.

Silent Air X-4 Air Pump, Aquarium Guys, Oct. 8, 2008, p. 1, http://www.aquariumguys.com/silentairpump4.html.

Whisper 60 Aquarium Air Pump, Aquarium Guys, Oct. 8, 2008, p. 1, http://www.aquariumguys.com/tetra-whisper60-air-pump.html.

Rena Air 400 Air Pump 702E, Aquarium Guys, Oct. 8, 2008, p. 1, http://www.aquariumguys.com/renaairpump4.html.

Tom Stellar Air Pumps S-30, Fish Tanks Direct, Oct. 8, 2008, p. 1, http://www.fishtanksdirect.com/index.asp?PageAction=VIEWPROD&ProdID=2102.

Aroma-Globe™ Essential Oil Diffuser/Nebulizer Diffuser World,Oct. 8, 2008, p. 1 http://www.diffuserworld.com/aromaglobATM-essential-oil-diffusernebulizer-p-10.html.

Nebulizing Diffuser, Betterherbs, Oct. 8, 2008, http://betterherbs.serrahost.com/Detail.bok?no=397.

Auroma Nebulizer for the House, Shop.com, Oct. 8, 2008, p. 1 http://www.shop.com/Auroma_Nebulizer_for_the_House_diffuser-46805905-p!.shtml.

Aura Cacia Electric Diffuser House Model, Shop.com, Oct. 8, 2008, p. 1, http://www.shop.com/Aura_Cacia_Electric_Diffuser_House_Model_diffuser-46805768-p!.shtml.

Essential Air Room Diffusers, Leyden House, Oct. 8, 2008, p. 1 http://www.leydenhouse.com/diffusers.html.

http://www.air-aroma.com/diffusers, Mar. 21, 2013.

http://www.prolitec.com/appliances_commercial.htm, Mar. 21, 2013.

http://scentair.com/why-scentair-solutions/, Mar. 21, 2013.

http://www.brandaroma.com/products/, Mar. 21, 2013.

http://www.e2aroma.com/appliances/smart-air-maxi/, Mar. 21, 2013.

http://www.scentaustralia.com.au/index.php/products/scent-diffuser-zephyr, Mar. 21, 2013.

http://www.voitair.com/scent-systems, Mar. 21, 2013.

http://www.fragrancemachine.com/, Mar. 21, 2013.

Spa Room Purilizer Assortment with instructions, http://www.sparoom.com/catalog/, webpage, Sep. 1, 2015.

Floracopeia, Inc., S3 Nebulizing Diffuser, User Manual Apr. 2015.

Shenzhen Jing Xin, Sharing Together Pure Aromatic Fresh Air Catalog, Apr. 2015.

Tom Stellar Air Pump W-60, Fish Tanks Direct, Oct. 8, 2008, p. 1 http://www.fishtanksdirect.com/index.asp?PageAction=VIEWPROD&ProdID=2104.

Pondmaster AP-60 Air Pump, Fish Tanks Direct, Oct. 8, 2008, p. 1 http://www.fishtanksdirect.com/index.asp?PageAction-VIEWPROD&ProdID02107.

* cited by examiner

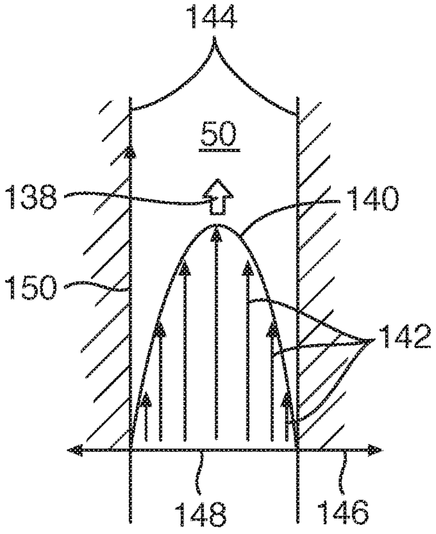
FIG. 14
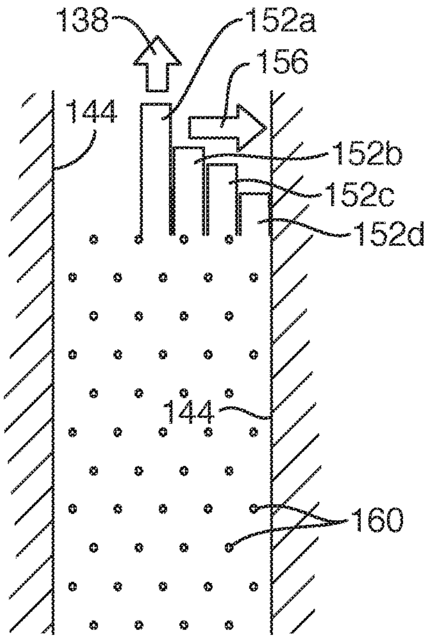
FIG. 15
$$N_{Re} = \frac{\rho V d}{\mu} \qquad 1$$
$$F_{Drag} = KAV^2 \qquad 2$$
$$F_{Drag} = M\Delta V = \Delta(MV) \qquad 3$$
FIG. 16

ANNULAR SEPARATOR APPARATUS AND METHOD

RELATED APPLICATIONS

This application claims the benefit of U.S. Provisional Patent Application Ser. No. 62/265,820, filed Dec. 10, 2015, which is hereby incorporated by reference in its entirety.

Additionally, this patent application hereby incorporates by reference U.S. Pat. No. 7,878,418 issued Feb. 1, 2011, U.S. Pat. No. 9,415,130 issued Aug. 16, 2016, U.S. patent application Ser. No. 14/850,789, filed Sep. 10, 2015, U.S. Provisional Patent Application Ser. No. 62/277,343, filed Jan. 11, 2016, and U.S. Provisional Patent Ser. No. 62/294,170, filed Feb. 11, 2016.

BACKGROUND

Field of the Invention

This invention relates to essential oils and, more particularly, to novel systems and methods for atomizing and diffusing them.

Background Art

Mechanisms exist for altering a closed environment such as a room or home with humidity. Likewise, mechanisms exist for removing humidity. Electronic and chemical mechanisms for destroying microbial sources of scents exist. Meanwhile, sprays, evaporators, wicks, candles, and so forth also exist to distribute volatile scents, essential oils, liquids bearing scents, and so forth. These may be introduced into breathing air, an atmosphere of a room, or any other enclosed space.

Heating often destroys or at least changes the constitution of essential oils. Thus, it has limitations. However, the evaporation rates or atomization rates of essential oils are often insufficient to provide a controllable, sustainable, and sufficient amount of an essential oil into the atmosphere. Thus, wicks having no air movement (convection) mechanism often prove inadequate in all those respects.

Meanwhile, mechanisms that seek to copy vaporizers and moisture atomizers often damage surrounding equipment, furniture, and other environs of a space being treated by essential oils. Moreover, the continuing "spitting" by atomizers of comparatively larger droplets not only causes damage to finishes on surrounding surfaces, but wastes a substantial fraction of the essential oil.

Essential oils are concentrated sources of aromas or scents. Their extraction from source plants is sometimes complicated, and always comparatively expensive, based on the cost per unit volume of the essential oil. Therefore, colognes, other fragrancing systems, and the like often use high rates of diluents for essential oils. They also use synthetic oils and artificial scents that may not replicate the comforting, familiar, and natural essence of essential oils.

By whatever mode, systems to distribute essential oils often waste an expensive commodity while damaging surroundings about their atomizers or other distribution systems. Thus, it would be an advance in the art to provide an apparatus and method for distributing essential oils in as small particles as possible, preferably vaporized, while protecting surrounding areas. It would be an advance to do so while retrieving and recycling for re-atomization or diffusion any droplets that are larger than those that may be sustained by effectively Brownian motion once discharged into surrounding air.

BRIEF SUMMARY OF THE INVENTION

In view of the foregoing, in accordance with the invention as embodied and broadly described herein, a method and apparatus are disclosed in one embodiment of the present invention as including a reservoir fitted with an extraction system for drawing out of the reservoir and feeding into a diffuser nozzle. The nozzle may operate as an eductor. In fact, in certain embodiments an eductor may include an injection nozzle feeding into a plenum which plenum feeds through a diffuser nozzle toward an ultimate discharge point or port.

In certain embodiments, a system may include separation or drift chambers. For example, an initial separation chamber may actually be an evacuated space or vapor space near the top of a reservoir. This provides the advantage of the reservoir directly relying on contact accumulation, coalescence by contact between an atomized spray and the content of essential oil in the reservoir.

Typically, an annulus of aspect ratio (length to width) of from 20:1 to 50:1 or greater may serve as a separator between this initial separation (drift) chamber, and other "downstream" separation (drift) chambers between the initial separation (drift) chamber and the ultimate discharge port. In various embodiments, lateral drift in laminar flow channels may separate out larger droplets for recycling. Changes of direction may also still serve as separation mechanisms. Thus, for example, the atomized flow composed of atomized essential oil and entraining air (air entraining those droplets and carrying them therewith) may pass as an atomized flow or simply flow through a circuitous route of passages.

Separator mechanisms may coalesce out comparatively larger droplets as they either drift into or strike with impact against solid surfaces. Solid surfaces may be naturally occurring walls of conduits, the reservoir, and so forth. However, surfaces may also be made up of baffles simply placed within a conduit or path in order to cause changes of direction, and to receive and coalesce overly large droplets. "Larger" means having too much mass, or rather too great a mass-to-surface-area ratio to drift indefinitely in air. This may also be expressed as a volume-to-surface-area ratio.

For example, a sphere has a volume. That volume is related to a third power of radius of the sphere. Thus, four thirds it multiplied by the radius to the third power equals the volume of a sphere having a radius of r. Meanwhile, the area of cross section (which controls air drag) is related to a second power or square of the radius. Surface area of the sphere is also related to the square of the radius.

Thus, one can see that cross sectional area and surface area increase as the square of radius. Volume (proportional to mass and gravity force) increases as the cube. This means that as radius increases, mass, as well as momentum and gravity force, increase at a greater rate than areas (proportional to drag) increase.

Conversely, this means that the decrease of radius decreases surface area as the square of radius, while decreasing volume as the cube of radius. Accordingly, there comes a point at which the cross sectional area controlling fluid drag of droplets in air is sufficiently large yet the mass and volume are sufficiently small, that a particle of such size may remain suspended indefinitely in air. That is, the drag forces resisting drift of the droplet downward with the force of gravity is sufficient to maintain indefinitely the drift of that droplet with the movement of air. Stated another way, the gravitational force is so miniscule as to be irrelevant to the time of drift. Gravity is unimportant. Drift can proceed effectively indefinitely.

Evaporation is an entirely different mechanism. In evaporation, individual molecules of a liquid become individual molecules of vapor. Vapors then abide by Dalton's law of partial pressures and take their place with other surrounding vapors including air, constituted primarily by oxygen and nitrogen. Thus, evaporated portions of an essential oil have performed well their function of distributing into the surrounding air.

Meanwhile, droplets sufficiently small to remain airborne substantially indefinitely, despite gravity, have also achieved their mission to distribute in air. Droplets too large, and therefore, too heavy, cannot be sustained in surrounding air against drift downward under the force of gravity. By drifting down these become the culprits in waste of essential oils and the damage to surrounding surfaces on which droplets land.

Thus, in an apparatus and method in accordance with the invention, it has been found that various separators have proven effective to provide several key factors. For example, separation devices provide time. The time of passage or containment of a droplet within a separation chamber provides opportunity for comparatively larger droplets to drift toward any coalescing surface. By coalescing surface is meant a surface upon which overly large droplets may strike and coalesce with one another under the natural surface tension affinity that the essential oil has for itself.

Also, the separation chambers have inlets and outlets offering changes of direction and cross section. Moreover, barriers will intercept "comparatively larger" particles by serving as coalescing surfaces. Barriers may also redirect flows, thereby encouraging striking thereof by overly large particles.

Herein we will define overly large particles as particles that are larger, especially those more than an order of magnitude larger in diameter than self-sustaining (permanently drifting) droplets. Thus, permanently drifting droplets are defined as droplets of an atomized liquid that are sufficiently small that they will not drift downward, especially the height of a room within a day of eight to twenty four hours. Thus, the finest particles, defined as permanently drifting particles are those whose gravitational acceleration under the force of gravity is insufficient to drift down.

Of interest also is any droplet that will not descend the height of a room within a day due to the resistance to drifting down by the fluid drag of the surrounding gases, such as room air. As a practical matter, droplets larger than these finest or permanently drifting particles are sufficiently small if they will drift with an airflow and leave with ventilation air. Often, air leaves a room in a matter of less than an hour.

For example, the American Society of Heating, Refrigerating, and Air Conditioning Engineering (ASHRAE) defines standards for room ventilation. Finest particles will necessarily be drifting with the flow of air and will leave a room before they have substantial opportunity to drift to the floor. Moreover, because room air is exchanged so frequently, typically more than once per hour, particles that are an order of magnitude larger than the finest particles also fit within the definition of comparatively smaller particles. In other words, these stay aloft for sufficient time to be swept out with the circulation of room air.

What is needed is a compact system to accomplish atomization and separation of the comparatively larger particles that can drift to the ground in less than an hour or less than an air exchange time. The size may vary with temperature and with the specific gravity (density compared to the density of water) of a particular essential oil.

Thus, an apparatus and method in accordance with the invention may rely on a compactly packaged, annular separation chamber. They may include drift chambers also in the flow path. The annulus provides drift time and a smooth flow separation mechanism for comparatively larger particles to drift toward and coalesce against annulus surfaces.

In one embodiment, a parallel eductor, which is effectively a coaxial eductor, operates to inject or atomize a plume of educted gas or vapor (e.g., air) starting as a jet entraining therewith a certain amount of an essential oil to be atomized. This jet, proceeding out of the jet nozzle or injection nozzle (which initiates and creates the jet), passes through a receptacle or well. The well is drawing the essential oil out of the reservoir, through a tube into that receptacle.

The jet of air passing through the essential oil entrains a certain portion thereof, or entrains an essential oil at a rate and with sufficient energy to strip droplets from the surface of surrounding essential oil. It ejects those droplets with the jet through a diffuser nozzle.

Of course, according to the laws of physics and engineering, droplets are generated in a variety of sizes. Initially, the largest of the comparatively larger droplets will not be able to make the turn required to reverse direction. Reversal is required in order to pass back out through the cap and a channel in the cap that exits the vapor space above the reservoir.

The effect of this parallel or quasi co-axial injection is that the first coalescing surface that the comparatively larger droplets strike is not a surface of a solid at all. It is the upper surface of the supply of essential oil restored in the reservoir. This provides highly effective coalescence. It results in a comparatively large ongoing momentum transfer from comparatively larger droplets into the upper surface of the essential oil in the reservoir.

Effectively, this may also entrain air into the upper surface, causing a certain amount of bubbling or foaming at the upper surface of the essential oil in the reservoir.

Conservation of mass principles at work require that the air used for the jet in the eductor pass out of the vapor space in the reservoir. At least one channel is provided for that purpose. Meanwhile, there may exist a random action or trajectory of an overly large droplet toward any of the walls of the reservoir. Above the line or surface of the contained essential oil, this may result in those walls becoming coalescing surfaces. After coalescing overly large droplets, the walls continue draining them back into the essential oil contained in the reservoir.

The full change of direction, about 180 degrees, from the injection direction toward the surface of the essential oil to the pathway out through the exit channel, represents a first separation process. It includes a direct-contact coalescence process. Some droplets may have direct contact with the content of the reservoir rather than coalescing with one another as each is smeared by impact against a coalescing surface. Thereafter a comparatively long annular channel relies on laminar flow, instead of turbulent flow to drift larger droplets toward its walls to coalesce and return to the reservoir.

Applicant hereby incorporates by reference: U.S. patent application Ser. No. 12/247,755, filed Oct. 8, 2008, issued Feb. 1, 2011, as U.S. Pat. No. 7,878,418, U.S. Design patent application Ser. No. 29/401,480, filed Sep. 12, 2011, issued May 29, 2012, as U.S. Design Pat. No. D660,951; U.S. Design patent application Ser. No. 29/401,517, filed Sep. 12, 2011, issued Sep. 4, 2012, as U.S. Design Pat. No. D666,706; U.S. patent application Ser. No. 13/854,545, filed Apr. 1, 2013; U.S. patent application Ser. No. 14/260,520, filed Apr. 24, 2014; U.S. Design patent application Ser. No. 29/451,750, filed Apr. 8, 2013, U.S. Design patent application Ser. No. 29/465,421, filed Aug. 28, 213; U.S. Design patent application Ser. No. 29/465,424, filed Aug. 28, 2013; and U.S. patent application Ser. No. 14/850,789, filed Sep. 10, 2015.

Each of these references, incorporated by reference herein in its entirety, discloses certain structures, components, controls, operating mechanisms, and designs for eduction and separation. In this application, Applicant need not, indeed cannot, reiterate all of the disclosure and illustrations contained therein. However, those references discuss various sizes and shapes of reservoirs, various types of caps and seals, various separation chambers, various striking surfaces or coalescing surfaces, and various paths and separation chambers. Those words are not necessarily used. Therefore, Applicant will hereby seek to define what is meant by these terms.

By a reservoir is indicated a supply, or a container for holding a supply, of an aromatic substance, such as an essential oil. By a diffuser is meant a system for atomizing and distributed comparatively smaller particles, including finest particles as defined hereinabove, and suitably fine particles that are within about an order of magnitude of the same diameter or radius as finest particles.

A jet is defined as in engineering fluid mechanics. A jet represents a flow of fluid having momentum, and passing through another fluid which may have the same or a different constitution. Thus, an air jet may pass through a surrounding oil. An air jet may pass through surrounding air. A significant feature of a jet is that it passes fluid having momentum through another fluid having a different specific momentum. Accordingly, momentum is exchanged between the environment and the jet, causing the jet to grow in size as a "plume." A plume will decrease in velocity as the momentum is distributed among more actual material (mass).

An eductor is a specific type of fluid handling mechanism. An eductor is a system in which a jet of a first constitution is injected into another fluid, typically of a different constitution. The momentum from the first jet is sufficient to cause the surrounding fluid entrained by the jet to continue as a plume of mixed constitution.

Herein, an eductor mechanism is created in which a jet, the source of that jet, and the surrounding environment into which the jet is injected are passed through an aperture. Any portion of the jet that exceeds the diameter or maximum dimension across the nozzle cannot pass therethrough, and thereby must recirculate back to be re-entrained in the jet, or to some other disposition.

A diffuser is in some respects an atomizer, but has the specific objective of producing finest fluid particles or droplets. Accordingly, a diffuser system includes not just an eductor but separation chambers, sometimes distinct separator structures. All are calculated to remove comparatively larger droplets, leaving only finest droplets and those within an about an order of magnitude thereof. Again, finest droplets or particles and comparatively larger particles have been defined hereinabove, in terms of their fluid dynamic behaviors. Those behaviors are defined by well established engineering equations. Therefore, all those equations are not repeated here. One may refer to textbooks and papers published on jets, atomization, fluid mechanics, two-phase flow, entrainment, plumes, and the like to obtain the details of the physics, the flow fields, the operational parameters, and governing equations for these phenomena.

Vapor space in a reservoir is defined as a portion of the volume of a reservoir container that contains other than predominantly the liquid for which the reservoir exists. That is, the vapor region actually contains air, a certain amount of the evaporated essential oil, according to Dalton's law of partial pressure in chemistry, and a certain quantity of drifting droplets in transit.

In certain embodiments of an apparatus and method in accordance with the invention, a reservoir may be fitted with an eductor injecting, through a diffuser nozzle, an entrainment jet containing both air, as the driving fluid, and atomized particles or droplets of the essential oil.

Mass flow rate is equal to an area times the velocity of material passing through that cross sectional area, multiplied by a density of the material flowing. Volumetric flow rate is simply a velocity of the flow rate multiplied by the cross sectional area through which that flow passes.

Whether looking at mass flow rate or volumetric flow rate, area is a controlling parameter. Increasing area, while keeping the volumetric flow rate constant, requires that the velocity slow down. Accordingly, in order to slow the velocity, area is increased. The result of a change in velocity is to permit more time for comparatively larger droplets to drift out of their entraining airflow toward any adjacent wall, baffle, or the like.

Accordingly, it has been found that diffuser systems or diffusion system in accordance with the invention, operating with the structures and fluid mechanisms in accordance with the invention, provide three valuable benefits not found in prior art systems. First, comparatively larger droplets do not exit the discharge port and drift down upon surrounding surfaces. Second, this effectively diffuses and controls, without heating, the amount of the essential oil diffused in order to provide a specific level of scent that is pleasant and effectively as strong as desired (controlled), without being overly strong.

Third, oil use required for a level of scent within a treated space has been shown to be much more efficient. That is, usage rates of less than half to a third of conventional systems result. Sometimes less than about one eighth to one tenth of conventional usage has resulted in systems in accordance with the invention.

In summary, the treated space has the properly controlled amount of the essential oil to provide the aroma and ambiance desired. Compared to prior art systems, whose rate of use is much greater, the essential oils are more efficiently used. Furniture and other surfaces are not damaged, sticky, or unsightly from comparatively larger particles drifting down onto them.

In various embodiments, a compact, integrated system may be placed within any arbitrary base or housing. It has been found that a reservoir may be fitted into virtually any décor.

Meanwhile, only electrical power crosses to the system from the arbitrary base. This results in pleasant possibilities for design, along with compactness, uniformity, and convenience of integration.

BRIEF DESCRIPTION OF THE DRAWINGS

The foregoing features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

FIG. 14 is a schematic diagram illustrating a velocity profile of fluid operating in a separator passage in a system in accordance with the invention;

FIG. 15 is an interpretive, schematic diagram thereof;

FIG. 16 is a chart identifying controlling equations for flow in the separation passage;

DETAILED DESCRIPTION OF THE PREFERRED EMBODIMENTS

Figure 1:
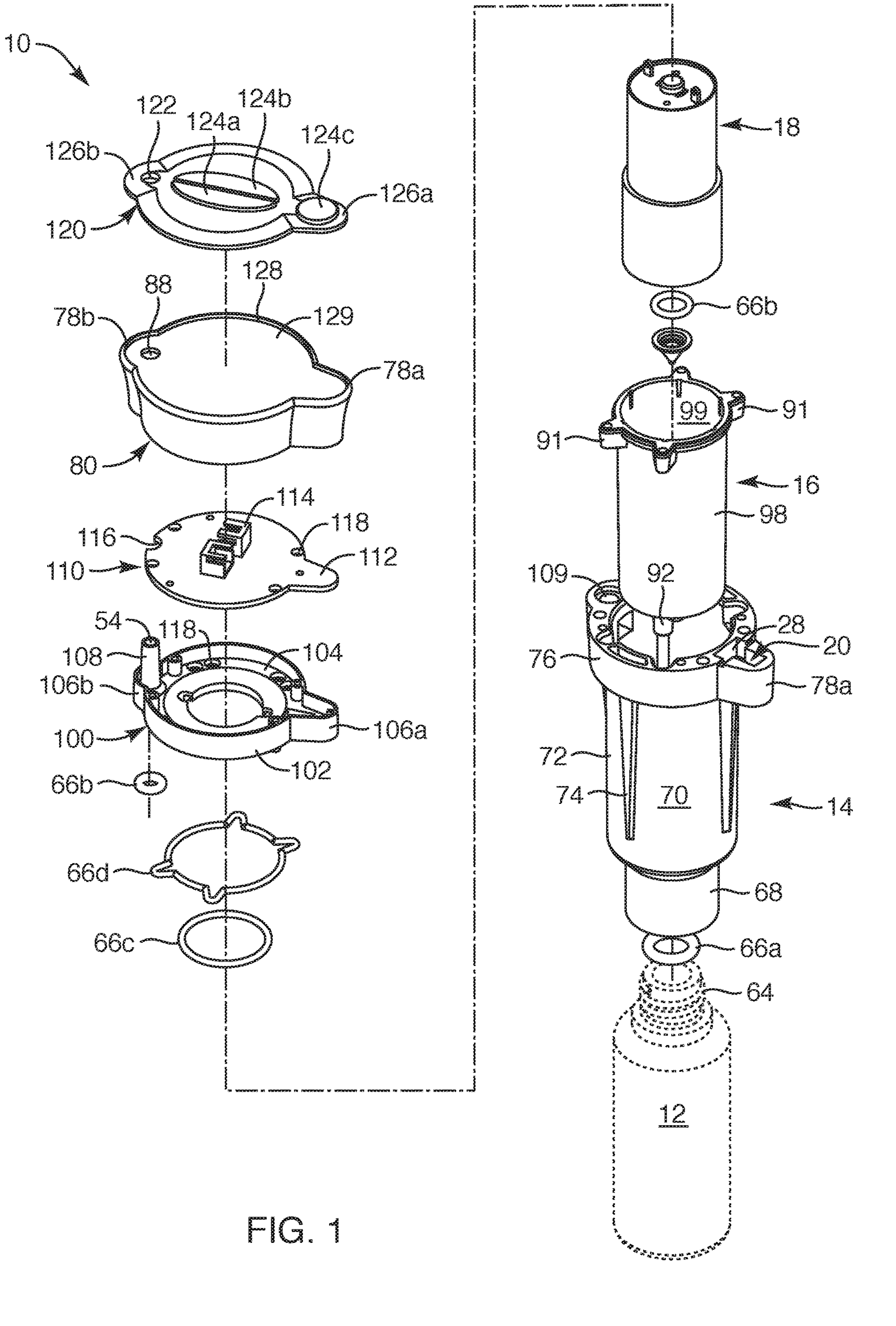
FIG. 1 is an exploded, perspective view of one embodiment of a system and apparatus in accordance with the invention.

It will be readily understood that the components of the present invention, as generally described and illustrated in the drawings herein, could be arranged and designed in a wide variety of different configurations. Thus, the following more detailed description of the embodiments of the system and method of the present invention, as represented in the drawings, is not intended to limit the scope of the invention, as claimed, but is merely representative of various embodiments of the invention. The illustrated embodiments of the invention will be best understood by reference to the drawings, wherein like parts are designated by like numerals throughout.

Figure 17:
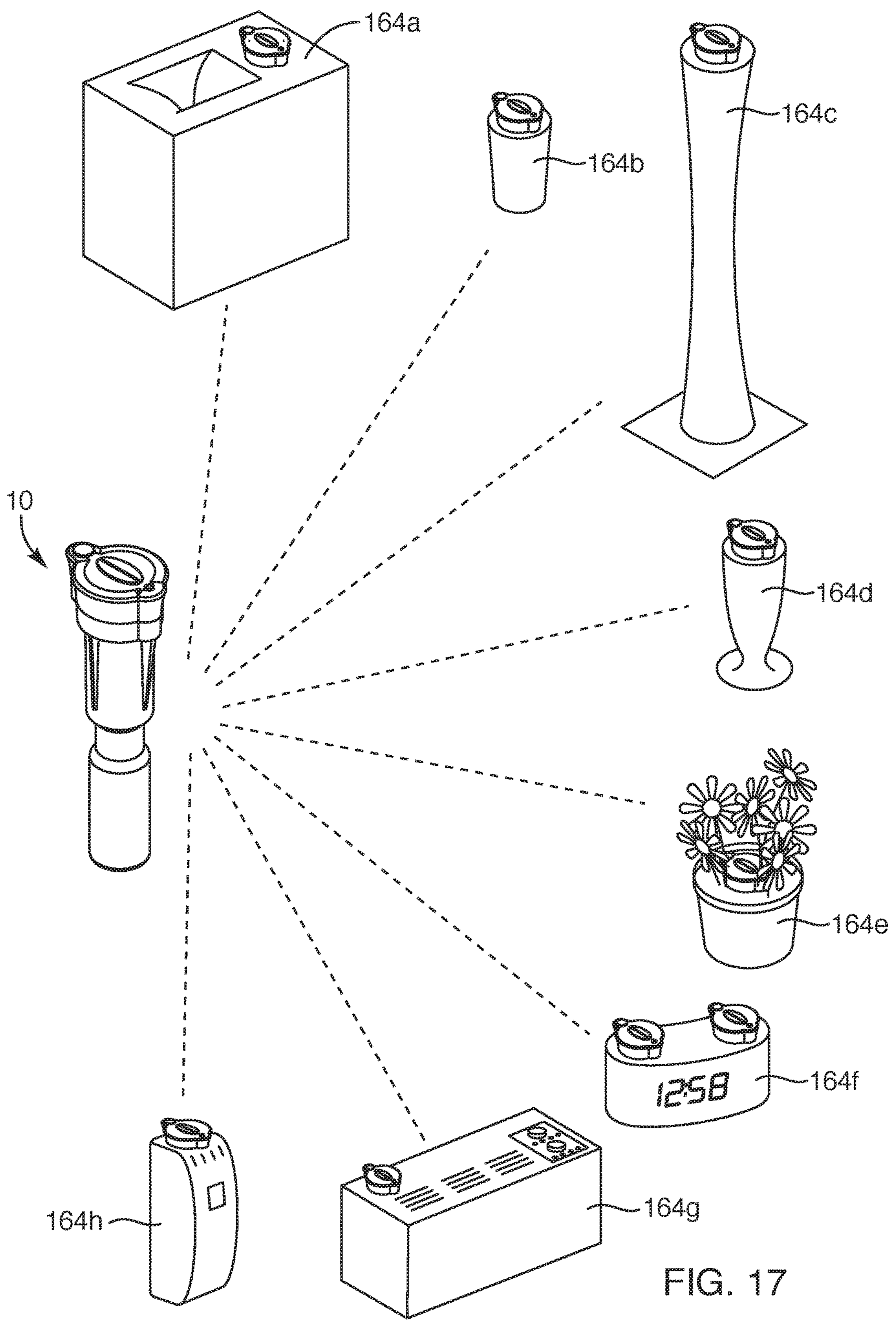
FIG. 17 is an exploded schematic diagram illustrating various alternative bases or holders for containing, hiding, or both, a diffuser in accordance with the invention.
Figure 18:
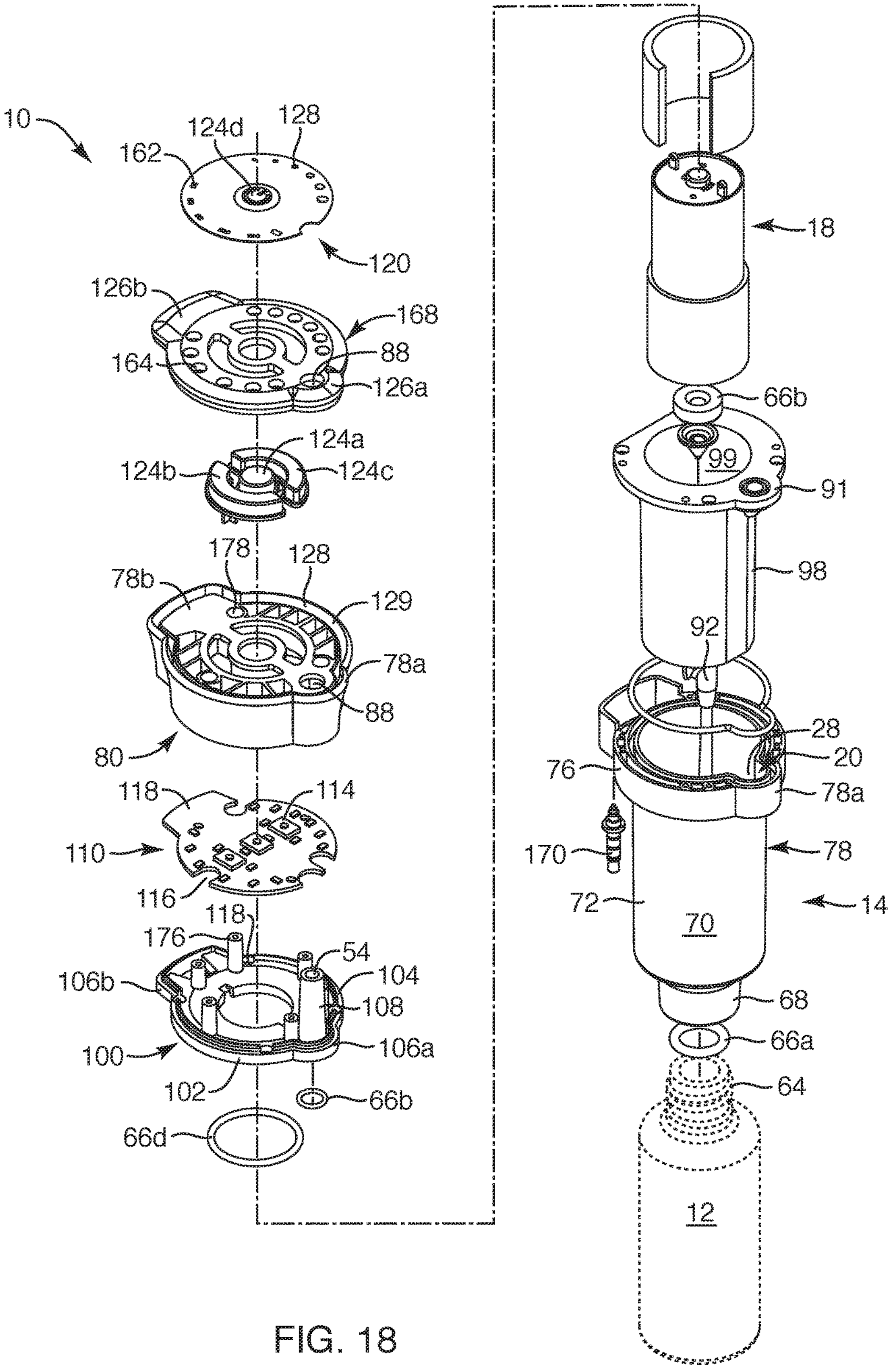
FIG. 18 is an exploded, perspective view of an alternative embodiment of a system in accordance with the invention.

Referring to FIG. 1 and FIG. 18, while referring generally to FIGS. 1 through 29, details of alternative embodiments of an apparatus and method in accordance with the invention are illustrated. In general, what applies to FIGS. 1 through 17 also applies to FIGS. 18 through 29. Thus, the embodiment of FIGS. 1 through 13 is one, concentric, annular diffuser. In contrast, the embodiment of FIGS. 18 through 29 is an alternative arrangement in which the sleeve 16 containing the drive 18 (the motor and pump system) is eccentrically mounted in order to increase the effective diameter (hydraulic diameter) of the passage 50 exiting the system toward the cap 80 and exit port 54. In that embodiment a channel has also been made inside the wall 86. Thus, most details of the embodiment of FIGS. 1 through 13 apply equally to the embodiment of FIGS. 18 through 29. Accordingly, all references to general principals and structures of either embodiment apply to each embodiment.

Referring to FIGS. 1 through 3, and 18-19 while continuing to refer generally to FIGS. 1 through 29, a system 10 in accordance with the invention may operate with a reservoir 12. In some embodiments, the reservoir 12 may be included as part of the system 10. In other embodiments, a system 10 may be adaptable to a variety of reservoirs 12, none of which need be an integral part of the system.

One reason for this is that reservoirs 12 may be standardized to a certain extent. Accordingly, various reservoirs 12 representing various brands of suppliers of the contents thereof may be manufactured in a variety of sizes, shapes, and so forth. Typically, a reservoir 12 will be adaptable to the system 10 regardless of the shape of the reservoir 12. At the very least, an adaptor may serve as an interface between a reservoir 12 and the remainder of a system 10. Thus, in a sense, the system 10 may act as a cap 10 on the reservoir 12.

In a system 10 in accordance with the invention, the system 10 may include several principal components, subsystems, portions, or regions. In the illustrated embodiment, a reservoir 12 connects to a housing 14. The housing 14 also receives inside of it, a sleeve 16, sometimes referred to as a motor sleeve 16 or a drive sleeve 16. Inside the sleeve 16 fits a drive 18 or drive system 18. It may be proper to refer to the drive 18 as the pump 18, the motor 18, the motive system 18, or the like.

The principal function of the drive 18 is to provide a flow of pressurized air. The drive 18 is connected to provide a flow of pressurized air to an eductor 20. A system of routes or passages is configured throughout the interior of the housing 14. Initially, air is drawn from the surrounding environment. Ultimately, a flow is discharged from the housing 14, adding a scent to the surrounding environment.

The initial intake of air or incoming flow is charged with comparatively very small particles of an essential oil or the like. These particles are then discharged in a flow of air into the surrounding environment. The scent may provide aromatherapy, mood scent, or other effects as a result of the scent of the particle introduced.

Figure 2:
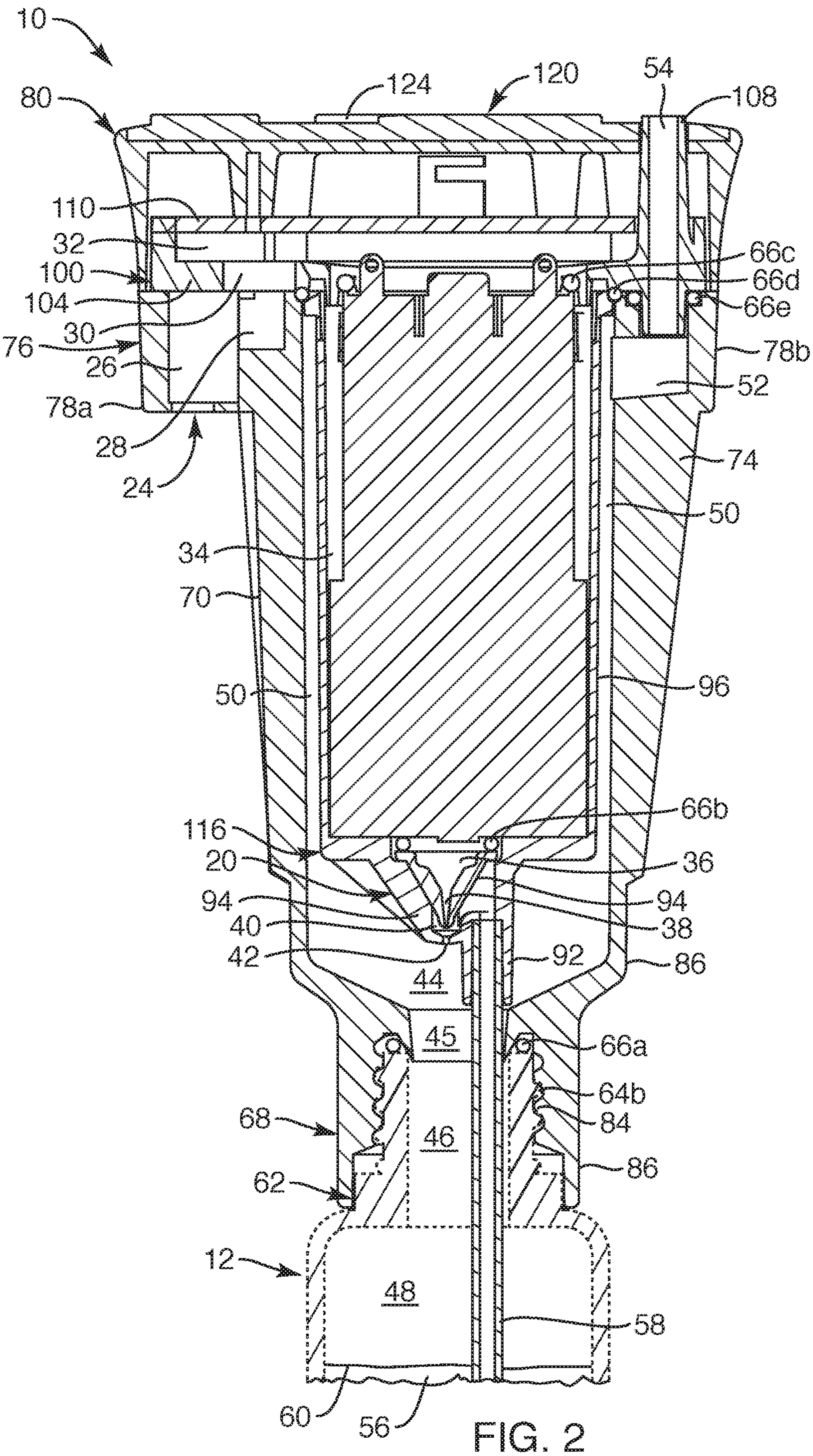
FIG. 2 is a cross-section, elevation view thereof.
Figure 19:
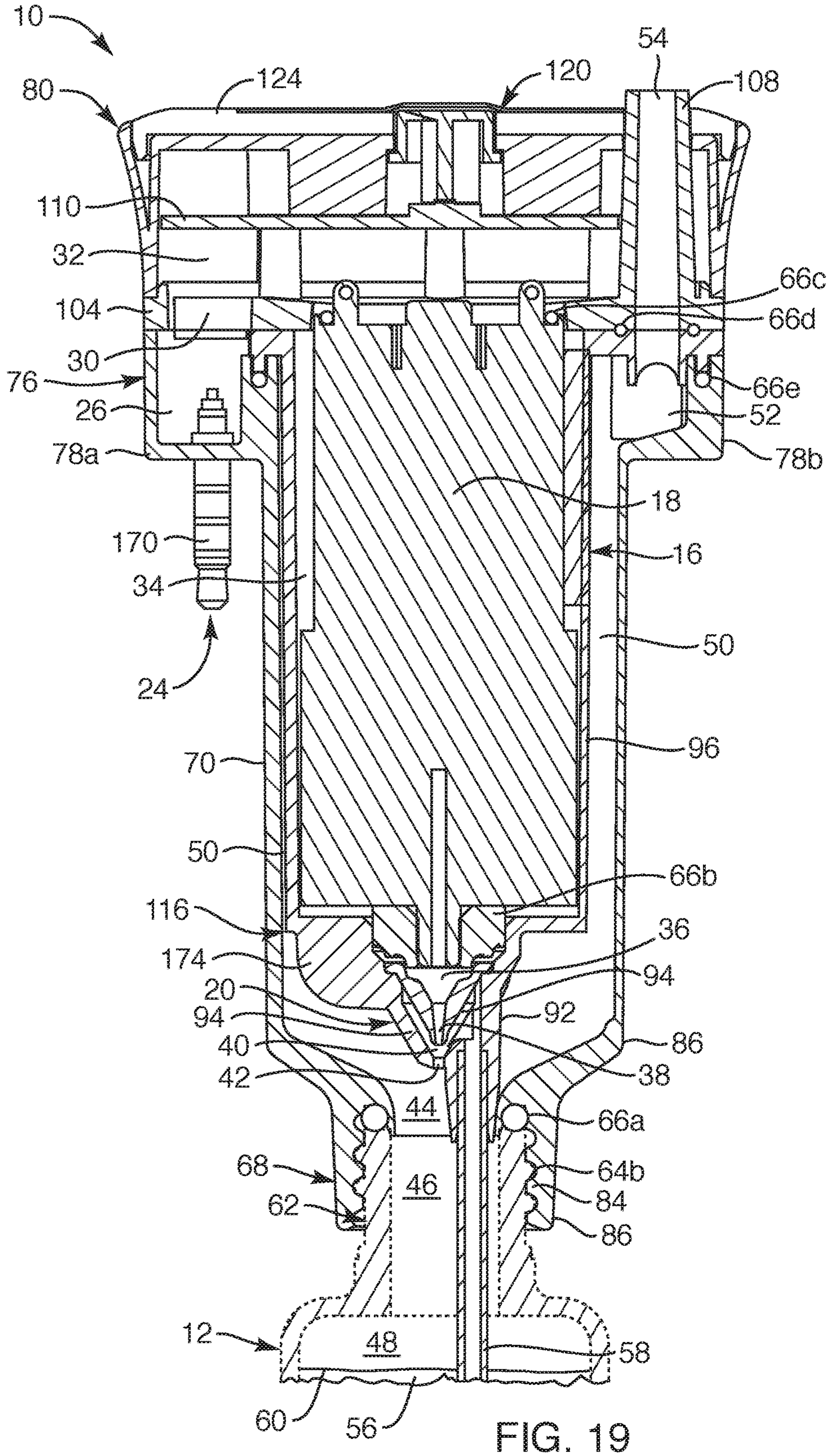
FIG. 19 is a side, elevation, cross-sectional view thereof in an assembled configuration.
Figure 20:
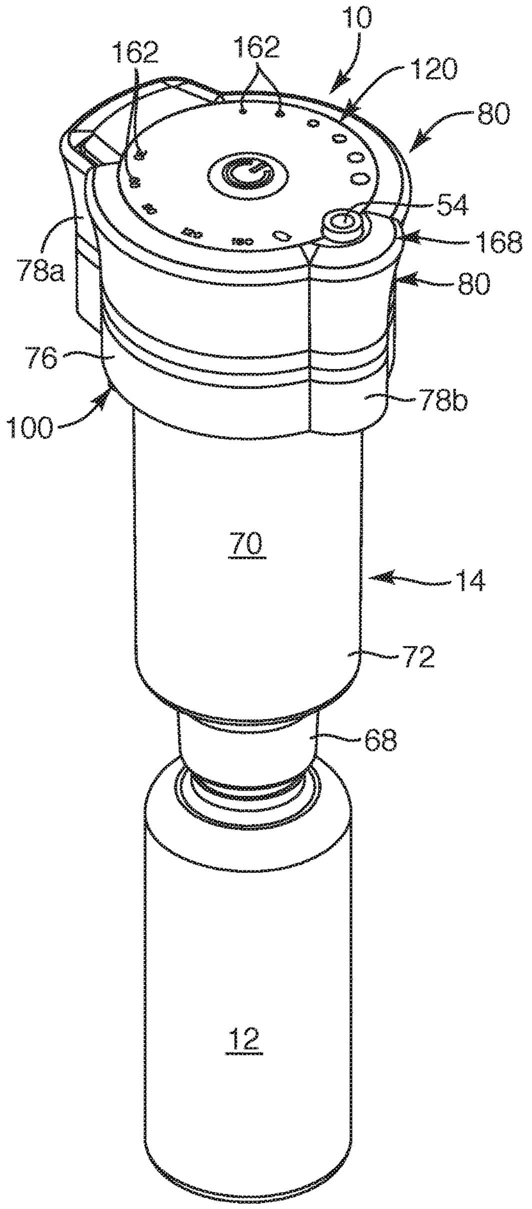
FIG. 20 is an upper, frontal perspective view thereof.
Figure 21:
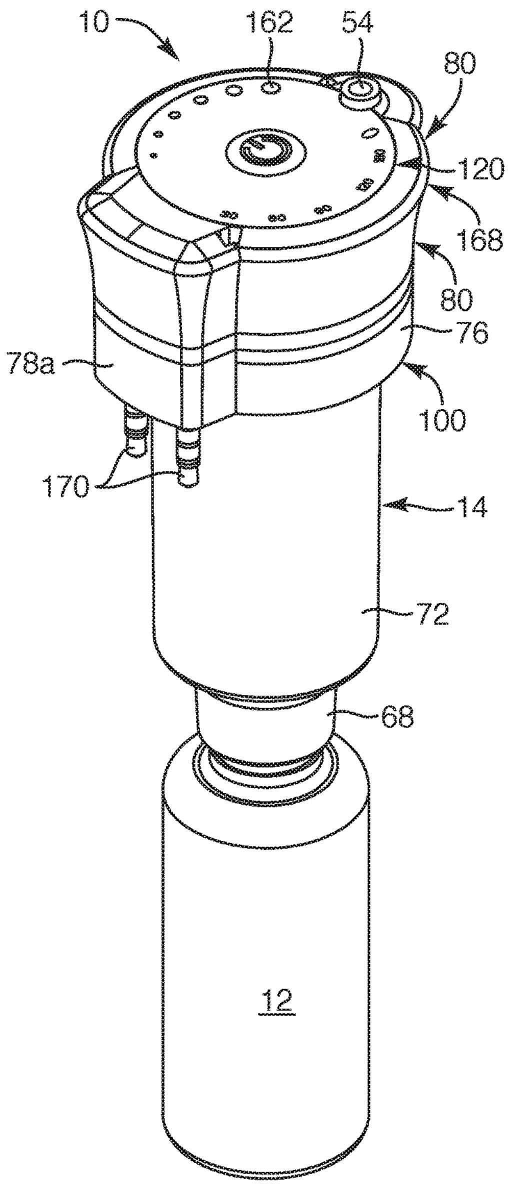
FIG. 21 is a upper, rear perspective view thereof.
Figure 22:
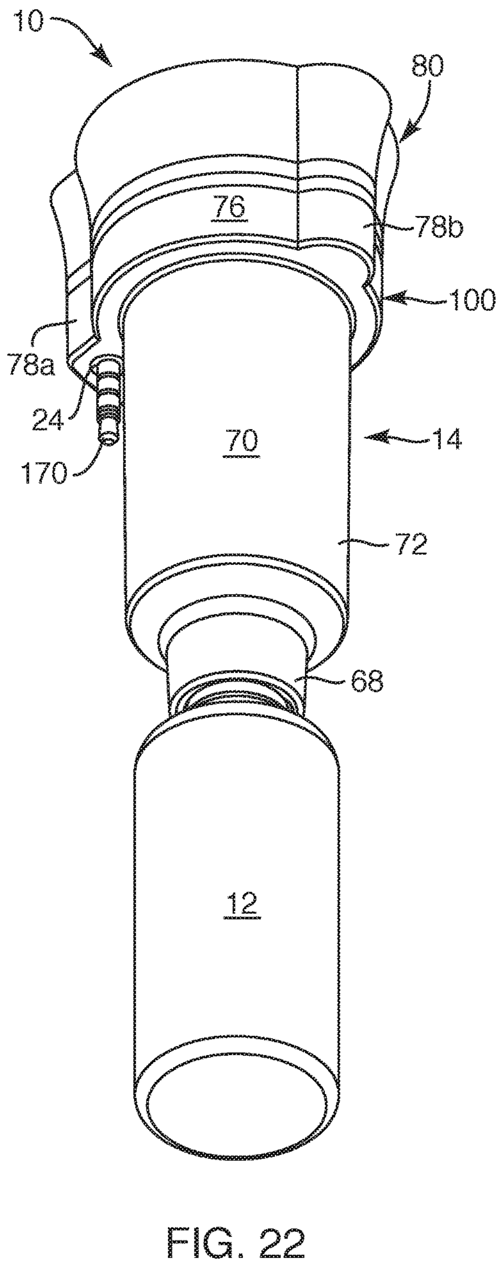
FIG. 22 is a lower, frontal perspective view thereof.
Figure 23:
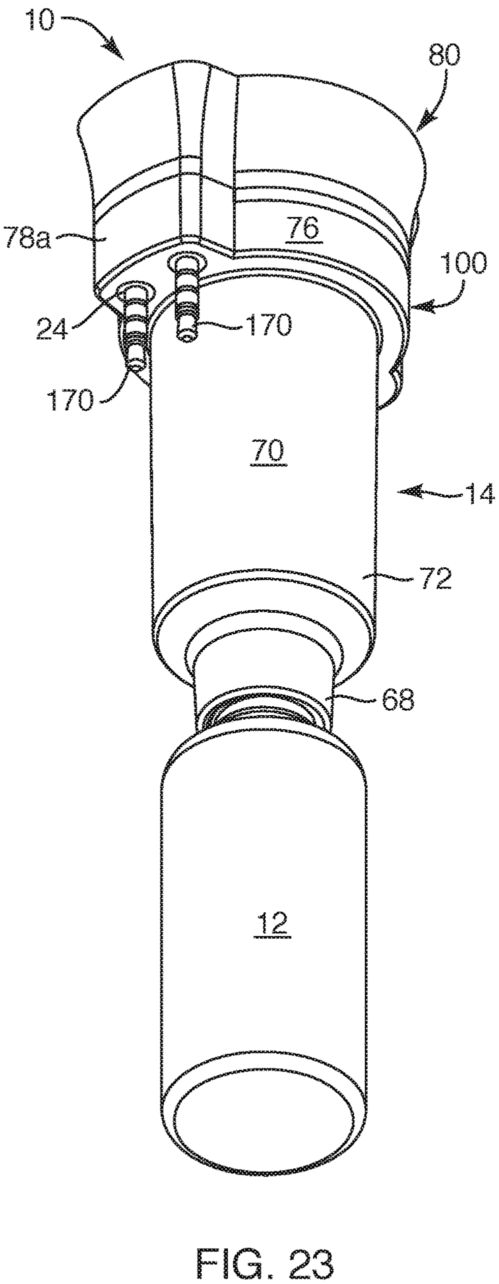
FIG. 23 is a lower, rear perspective view thereof.
Figure 24:
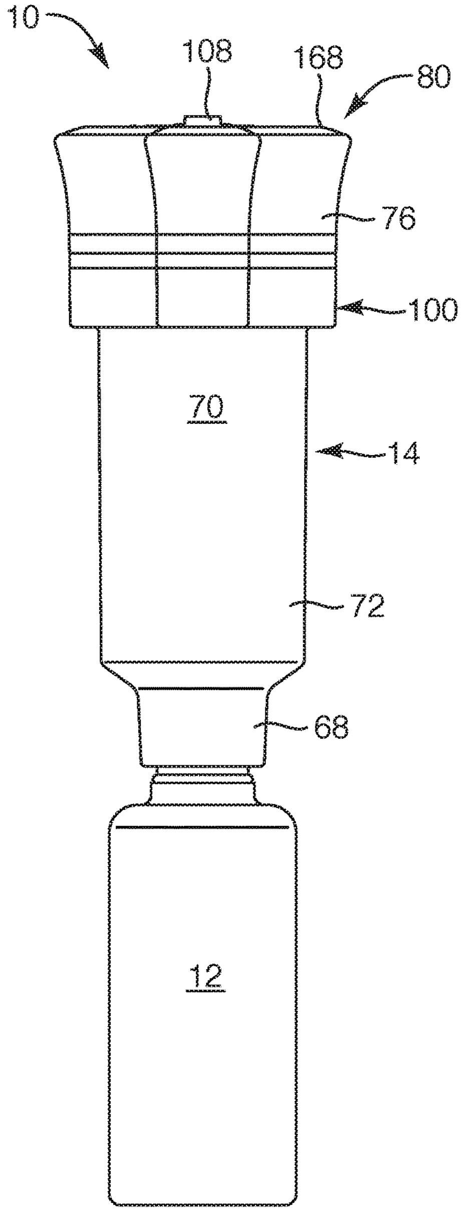
FIG. 24 is a front elevation view thereof.
Figure 25:
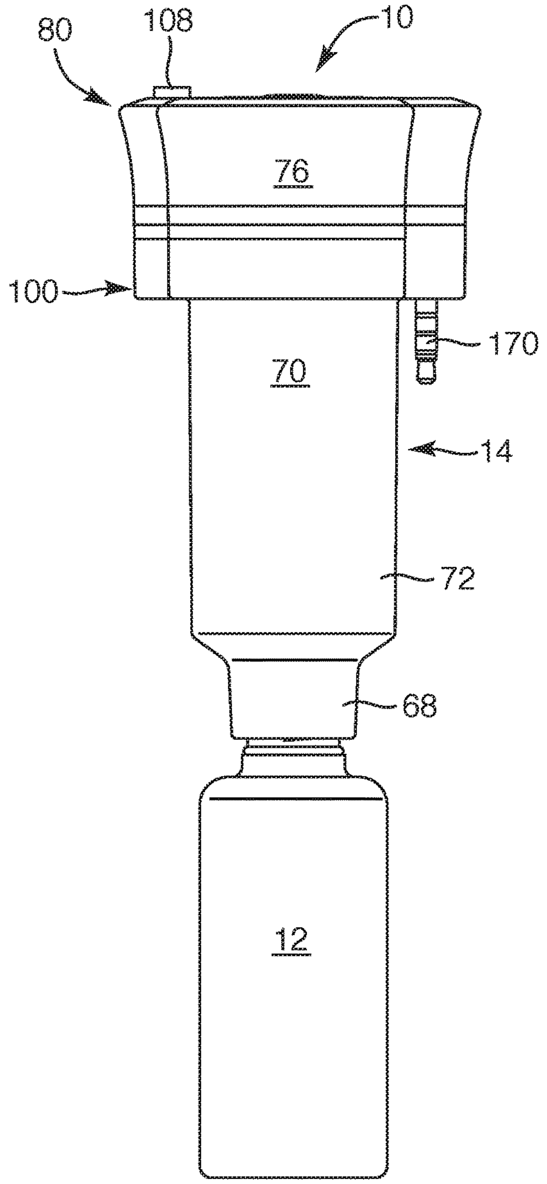
FIG. 25 is a right side elevation view thereof.
Figure 26:
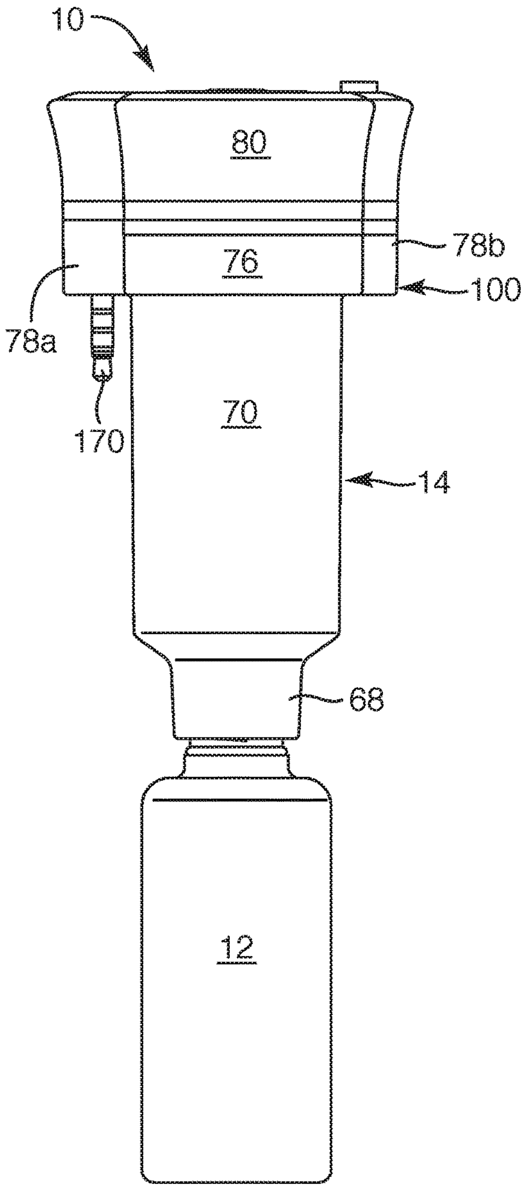
FIG. 26 is a left side elevation view thereof.
Figure 27:
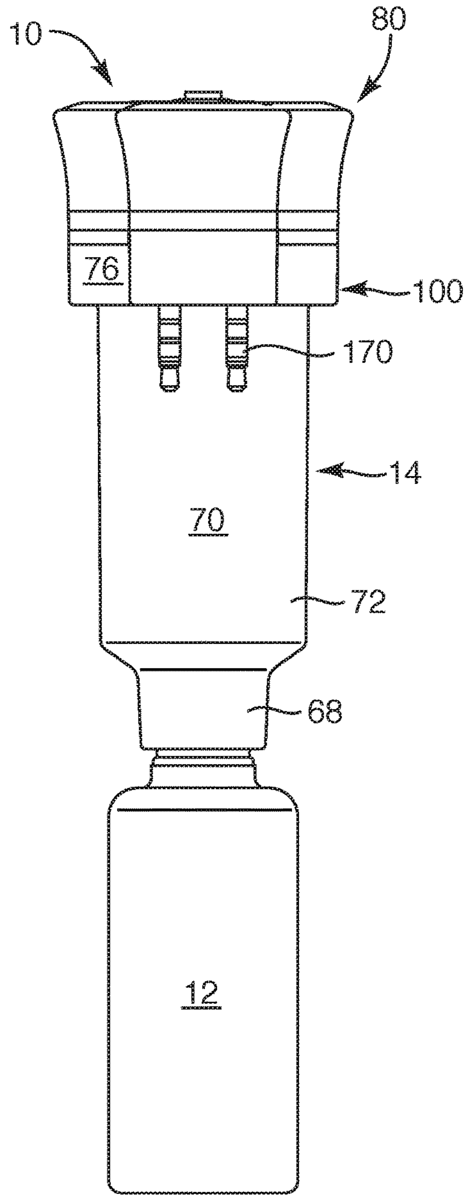
FIG. 27 is a rear elevation view thereof.
Figure 28:
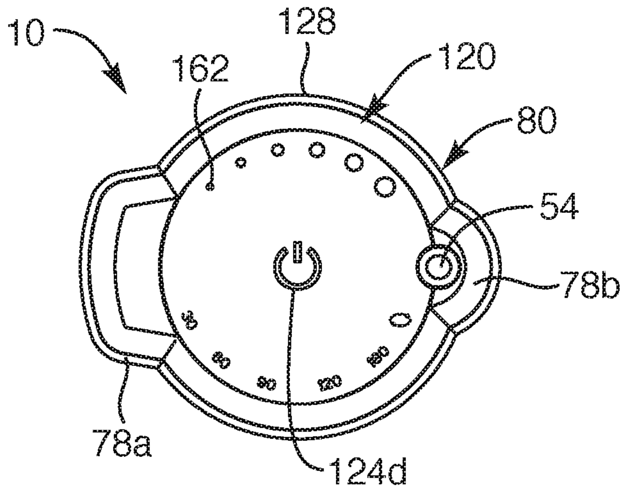
FIG. 28 is a top plan view thereof.
Figure 29:
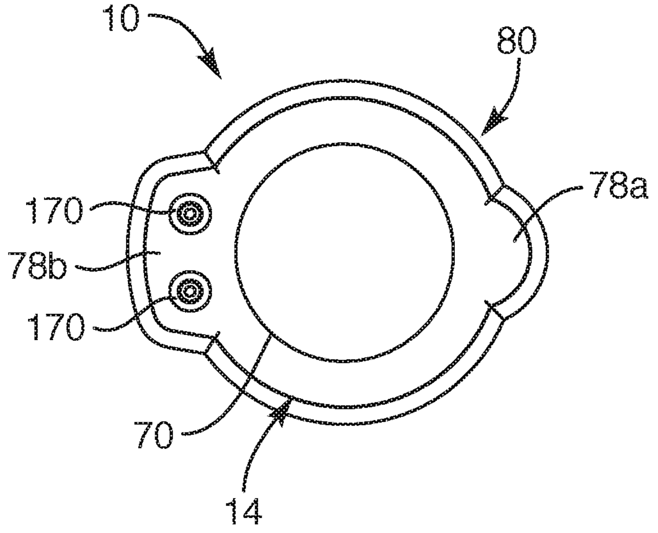
FIG. 29 is a bottom plan view thereof.

Referring to FIGS. 2 and 19, while continuing to refer generally to FIGS. 1 through 29, the inlet port 24 connects to an inlet chamber 26. The flow of air, initially untreated, and then ultimately carrying a scent begins its entry into the system 10 through an inlet port 24. From the inlet port 24, air next passes into an inlet chamber 26. The inlet chamber 26 may be provided with a filter, filter medium, or the like. Such a filter medium may fill the entire inlet chamber 26, or merely a portion thereof. In some embodiments, the filter medium may simply act as a gatekeeper against dust or other pollutants undesirable to be flowing through the system 10.

To arrive at the point of receiving an essential oil or other content of the reservoir 12, the flow of air in this particular example embodiment must pass from the inlet chamber to a transfer chamber 28. The transfer chamber 28 provides a region 28 that can align with a perforation 30 or transition passage 30 in order to access a plenum 32. The plenum 32 here is seen to extend across the housing 14. The plenum 32 supplies through one or more openings the incoming flow of air into a cooling passage 34. The passage 34 may be an annulus, multiple channels, or the like.

One will note that the cooling passage 34 or passages 34 may run effectively vertically or substantially vertically between the sleeve 16 and the drive 18. Accordingly, the cooling passage 34 passes a continuing flow of ambient air around the outside surfaces of the drive 18. Thus, the cooling passage 34 provides a certain degree of cooling to the drive 18.

The drive 18 includes electrical equipment and the use of electrical power. The drive 18 benefits substantially from the cooling effect of incoming air that can receive rejected heat. Rejected heat is a term of art in thermal engineering and is used here as such. The flow will continually absorb waste heat discharged or rejected by the drive 18, and carry that heat away. Thus, the enclosure by the sleeve 16 of the drive 18 still provides for continuing cooling by a continuing stream of outside or ambient air passing the drive 18.

From the cooling passage 34, the air is eventually drawn into a portion of the drive 18 pumping that air into a plenum 36. The plenum 36 now contains pressurized air pressurized substantially above ambient pressures.

For example, air at ambient pressure is drawn by a reduction of that pressure, caused by the drive 18. Thus, pressure is comparatively higher in the ambient than in the inlet chamber 26. Pressure is higher in the inlet chamber than the transfer chamber 28. Pressure is higher in the transfer chamber 28 than in the transition chamber 30 or the perforation 30. Meanwhile, air pressure in the plenum 32 is higher than pressure in the cooling passage 34. Pressure drops throughout the passage and through the cooling passage 34. Pressure continues to drop until the pump portion of the drive 18 suddenly increases that pressure. Upon pumping, pressure rises in the plenum 36 relative to the other passages 24, 26, 28, 30, 32, 34, 36.

From the plenum 36, a nozzle opening 38 passages a comparatively smaller cross-sectional area of air at a comparatively much higher velocity than that air has experienced prior thereto. In the environment, the air is substantially quiescent. Whatever air movement there may be is comparatively small. Depending upon the area or cross-sectional area in each of the passages 24, 26, 28, 30, 32, 34, 36, the velocity of the air will change. At the nozzle 42, the most restrictive (smallest) area results in a significant increase in velocity.

As a practical mater, the mass flow rate of air through any passage 24, 26, 28, 30, 32, 34, 36, 38 is equal to the density, times the cross-sectional area, times the velocity. Accordingly, at a mass flow rate that must be constant throughout, any increase of area along its path results in a decrease of velocity. Conversely, every decrease in area results in a proportional increase in velocity. Slight variations of density may occur, but are not significant.

The nozzle passage 38 injects high speed air into an eductor chamber 40. The eductor chamber 40 is extremely significant. The eductor chamber 40 receives the air from the nozzle 38. However, the eductor chamber 40 also permits "eduction" of surrounding air. Eduction is a process of momentum transfer. From a central jet, representing the air exiting the nozzle 38, the eductor chamber 40 provides a location wherein surrounding air within the eduction chamber 40 may be drawn in by the jet to be entrained in the jet. Thus, a jet exiting the nozzle 38 increases in size, and decreases in maximum velocity as it draws in surrounding air by eduction (direct momentum exchange) or entrainment.

As a result of this eduction or entrainment, a reduced pressure surrounding the jet out of the nozzle 38 exists within the eduction chamber. Accordingly, the content 56 or oil 56 from the reservoir 12 is drawn into the eduction chamber 40.

Ultimately, the pressure difference between the eductor chamber 40 and a drift chamber 44 causes the spray to pass through a spray nozzle 42. This spray nozzle 42 or eductor nozzle 42 stands in contrast to the air nozzle 38. Only air passes through the nozzle 38. In the eductor chamber 40, surrounding residual air and the content 56 or essential oil 56 from the reservoir 12 mix together. The drift chamber 44 operates at an even lower pressure, thus the comparatively higher pressure in the eductor chamber 40 drives a spray in two phases (liquid and gas) made up of the oil 56 or other content 56 in comparatively small droplets or particles entrained within the air injected by the air nozzle 38 into the eductor chamber 40.

The spray ejected by the spray nozzle 42 or eductor nozzle 42 enters the drift chamber 44 in a downward, vertical direction. This is by design. By injecting downward, the nozzle 42 encourages comparatively larger particles that are sufficiently large in mass (and therefor in weight) that are incapable of remaining entrained in the air flow to continue down through the neck 46 of the reservoir 12.

In fact, the neck 46 or neck passage 46 continues into a vapor space 48 near the top of the reservoir 12. Inasmuch as the vapor space 48 provides access to the oil 56, comparatively larger droplets may drift down into the reservoir 12 to be captured by the oil 56. Herein, oil 56 simply means the content 56 of the reservoir 12. In some embodiments, the content 56 may be exclusively oil. In others, the oil 56 may be dissolved by a solvent such as alcohol or water. In some embodiments, multiple types of oils 56 may make up the content 56.

In order to exit the vapor space 48, any air and entrained droplets must pass into an annulus 50 formed between the housing 14 and the sleeve 16. In some regards, the annulus 50 provides additional cooling and isolation of the drive 18. For example, the drive 18 is contained within the sleeve 16. The sleeve 16 and drive 18 provide the cooling passage 34 of incoming air serving to cool the drive 18.

Moreover, the annulus 50 passing back up between the housing 14 and the sleeve 16 provides an additional layer of cooling and isolation of the drive system 18 and the sleeve 16 from the outside environment. Thus, heat from the drive 18 may continue to be carried away by the flow through the annulus 50. The annulus 50 may be thought of as the passage 50 between the housing 14 and the sleeve 16. Also, it is proper to speak of the annulus as the portions of the sleeve 16 and drive 18 that form a passage 50 or annulus 50. For example, the annulus need not be entirely continuous about its circumference.

Eventually, flow must pass from the annulus 50 out through a final drift chamber 52 or transition chamber 52. The term drift chamber 52 refers to the fact that a two-phase flow necessarily includes both a vapor or gas and an entrained second phase (liquid here). The particles of the second phase are at liberty to drift. If they are sufficiently small, then the fluid drag imposed by the air (gas) on the second phase (e.g., oil) will be greater than the effect of gravity or the effect of momentum (due to velocity) of such a particle.

Accordingly, sudden changes of direction, sudden changes of cross-sectional area, and the like will result in the need for a particle to change speed, direction, or both. Otherwise it may be thrown against a solid surface and splatter, or coalesce, or do some of both. Thus, in a drift chamber, generally, changes of direction result in particles of the oil 56 striking a wall, and thereby being either comminuted into smaller particles or coalesced against the wall, to flow back down into the reservoir 12. By either mode, only those particles that are sufficiently small to change direction and speed rapidly enough to remain entrained within the air can be carried on to exit the housing 14. All other droplets will eventually find their way back to the reservoir 12.

Exiting the annulus 50, the flow passes through the final drift chamber 52 and ultimately an exit passage 54. As explained, multiple drift chambers 44, 52, as well as the drift passage 50 that is the annulus 50, provide the opportunity for comparatively larger droplets to drift out of the flow. Those drifting out may shatter. All particles that cannot remain entrained must re-shatter or else coalesce against surrounding solid surfaces. This effectively filters or sorts the particles, thereby leaving only the comparatively smallest to exit out of the exit passage 54 into the surrounding environment.

In the second phase (liquid) material, the content 56 or oil 56 in the reservoir 12 is drawn into a siphon tube 58. The tube 58 extends below the surface 60 or liquid levels 60 of the content 56 in the reservoir 12. The tube 58 here illustrated must necessarily pass up through the neck 62 of the reservoir 12 into the eductor chamber 40. In the eductor chamber 40, the comparatively high speed air blasting from the nozzle 38 fractures the flow of oil 56 into droplets entrained by the air flow and injected through the eductor nozzle 42 into the drift chamber 44.

The reservoir 12 may be connected to the housing 14 by threads 64 on the outer surface of the neck 62 of the reservoir 12. A seal 66 between the neck 62 and the housing 14 may be both liquid tight and air tight.

In general, a reservoir 12, and more particularly, the threads 64 and neck 62 of the reservoir 12 may be received into a receiver 68. The receiver 68 may be thought of as a receiver portion 68 of the housing 14. In general, the body 70 of the housing 14 includes the barrel portion 72 that operates as the bulk of its containment. The receiver 68 necks down to a comparatively smaller diameter in order to fit the threads 64 and neck 62 of the reservoir 12. Meanwhile, ribs 74 may be added for one of several reasons. Typically, the ribs 74 will provide additional strength, and, more importantly, stiffness stabilizing the body 70 or the shape of the body 70. Thus, less material is required in the body 70 if the ribs 74 are spaced periodically to provide increased stiffness and strength.

Opposite the receiver 68 at the bottom end of the body 70 is the collar 76. The collar 76 is very much a business end 76 of the body 70 of the housing 14.

For example, an inlet lobe 78*a* accommodates the inlet chamber 26. In other words, the inlet lobe 78*a* effectively has the inlet chamber 26 formed therein. Meanwhile, an outlet lobe 78*b* provides space for the exit passage 54 to pass, or otherwise connect to the annulus 50 or annular separator 50.

A cap 80 is the complement to the body 70, sealing the body 70 to form the overall housing 14. The cap 80 is fitted to the collar 76. In fact, the collar 76 is provided with relief spaces 82 or sockets 82. Those sockets 82 receive and register portions of the sleeve 16 fitted thereto.

Similarly, at the opposite end of the body 70, away from the cap 80 on the collar 76, threads 84 match the threads 64 on the reservoir 12. Again, the seal 66*a* serves to seal the neck 62 of the reservoir 12 against the receiver 68 of the housing 14. Various other seals 66 are seen throughout the system 10.

The wall 86 of the body 70 extends along the receiver 68 and the barrels 72. The wall 86 becomes somewhat more complex as it extends to form the collar 76.

An outlet 88 or aperture 88 formed in the cap 80 permits passage of scented air or a flow of scented air from the system 10 into the environment. The penetration 88 or aperture 88 in the cap 80 permits that passage. Thus, substantially all air into the system 10 must enter through the inlet port 24 in the collar 76 of the body 70 of the housing 14. Substantially all fluid, meaning entrained particles and their entraining air will pass out of the system 10 by way of the outlet 88 or aperture 88 in the cap 80 sealing the system 10. Any droplets coalescing against solid surfaces flow back to the reservoir 12.

Figure 3:
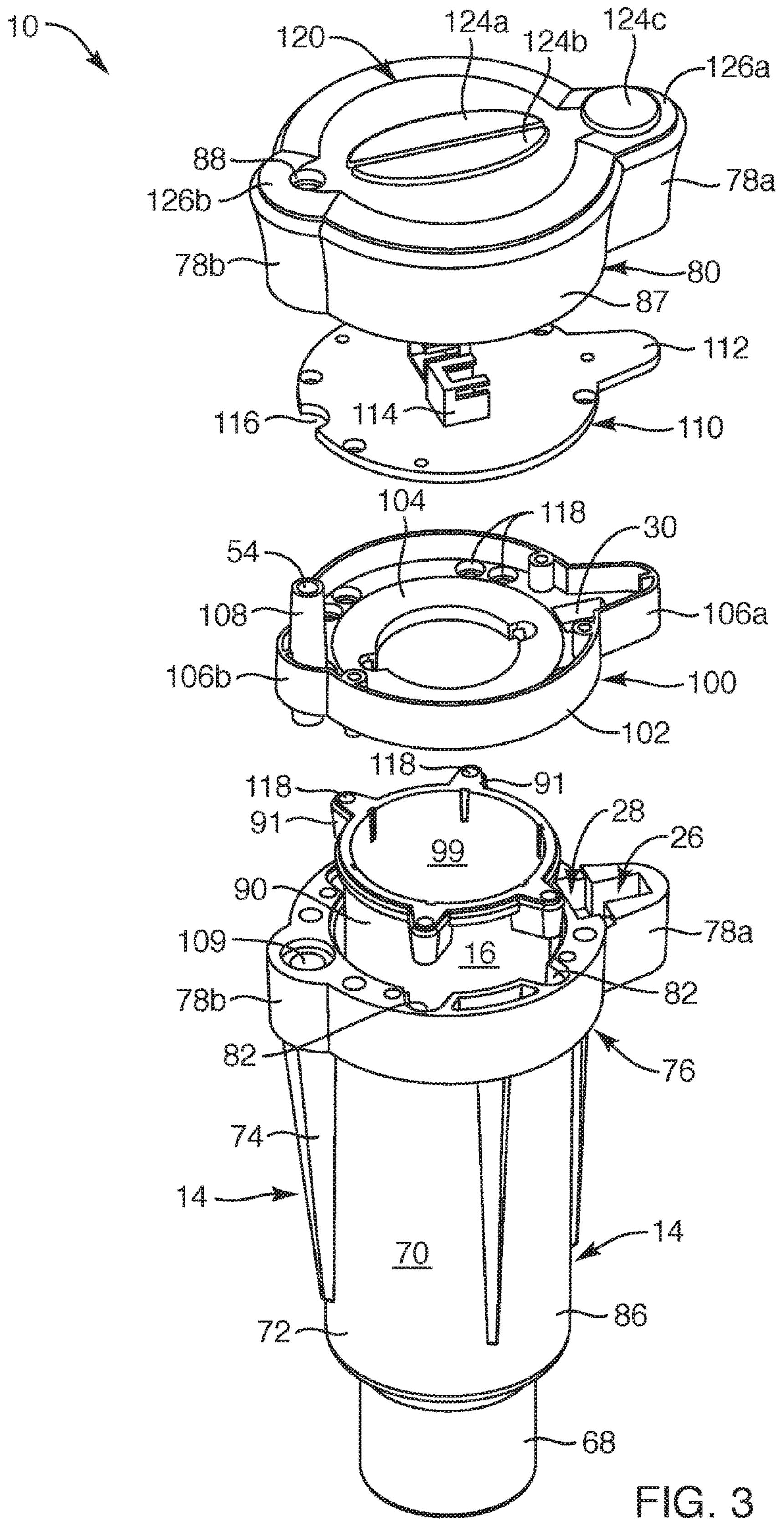
FIG. 3 is a partially exploded, perspective view thereof, absent the reservoir.
Figure 4:
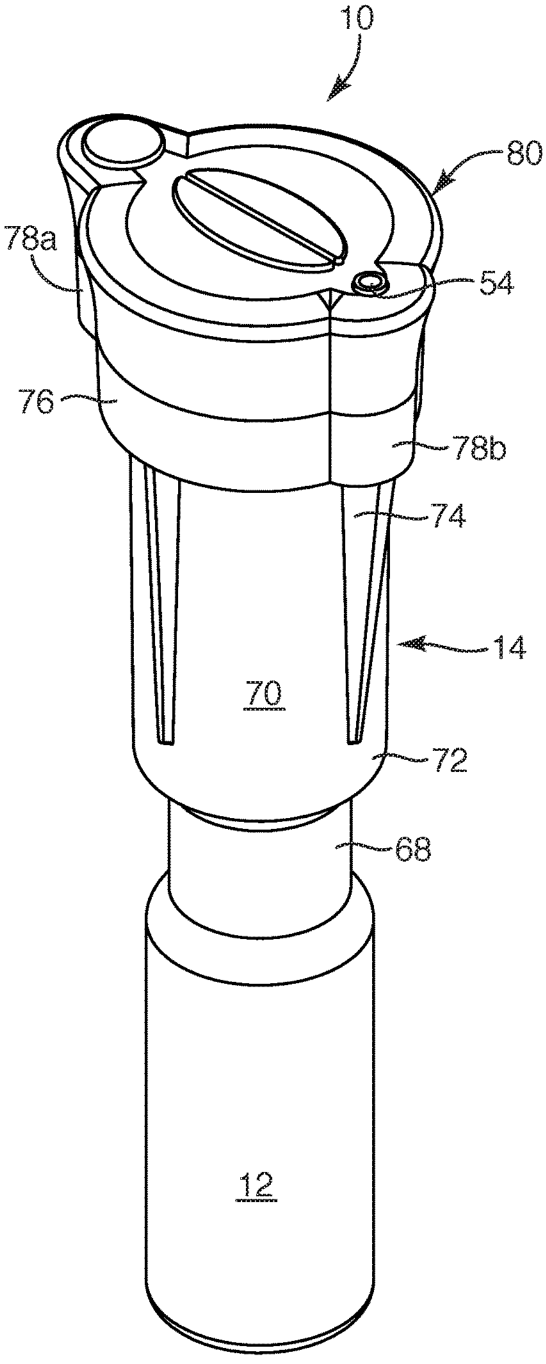
FIG. 4 is a perspective, assembled view thereof from the outlet side of the diffuser.
Figure 5:
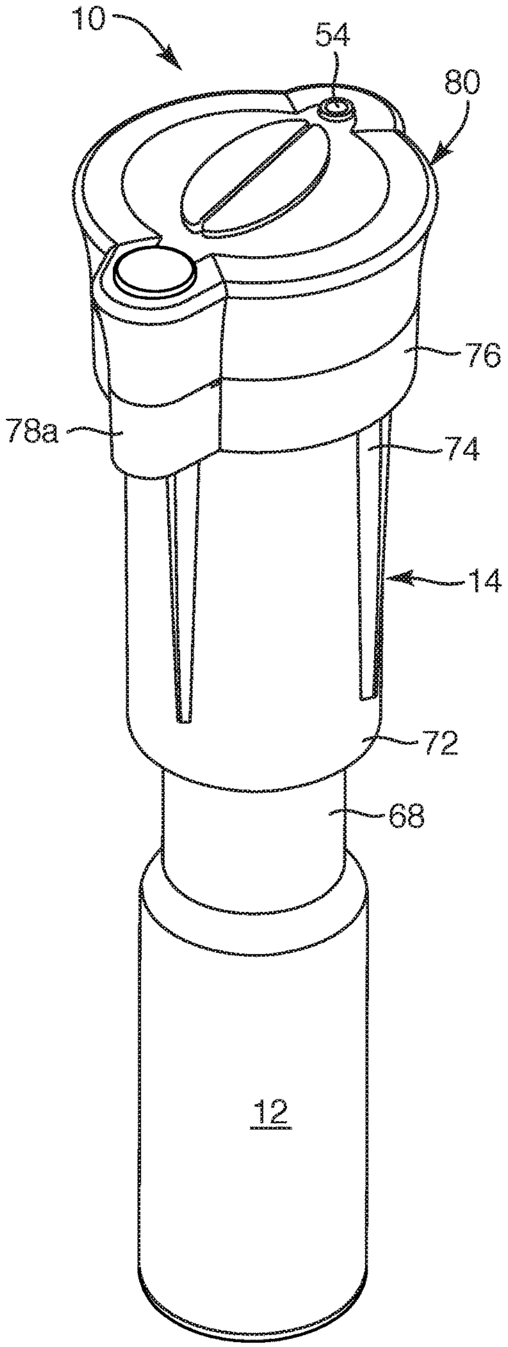
FIG. 5 is a perspective view thereof from the air inlet side thereof.
Figure 6:
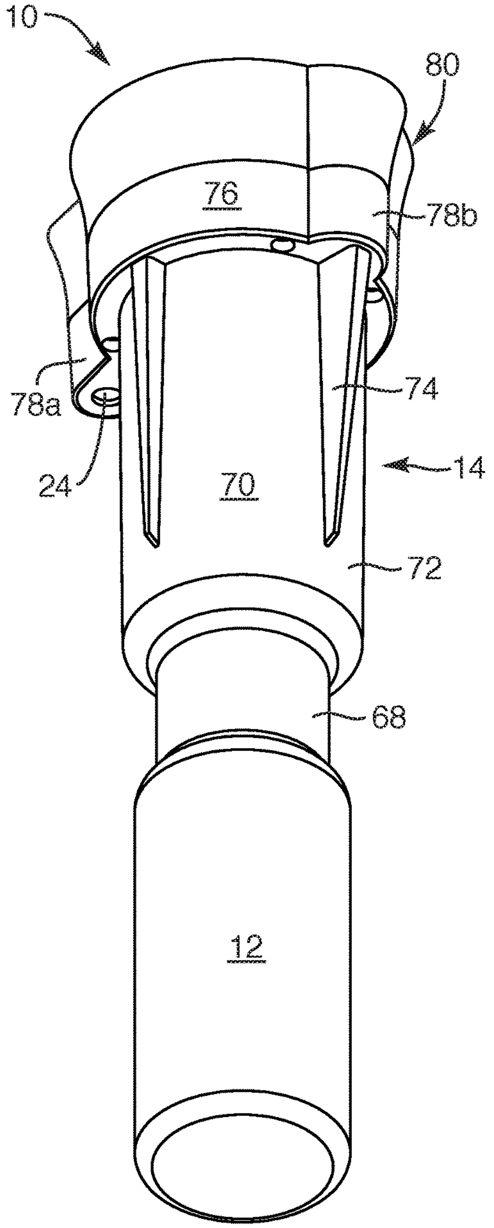
FIG. 6 is a lower quarter perspective view thereof from the outlet side thereof.
Figure 7:
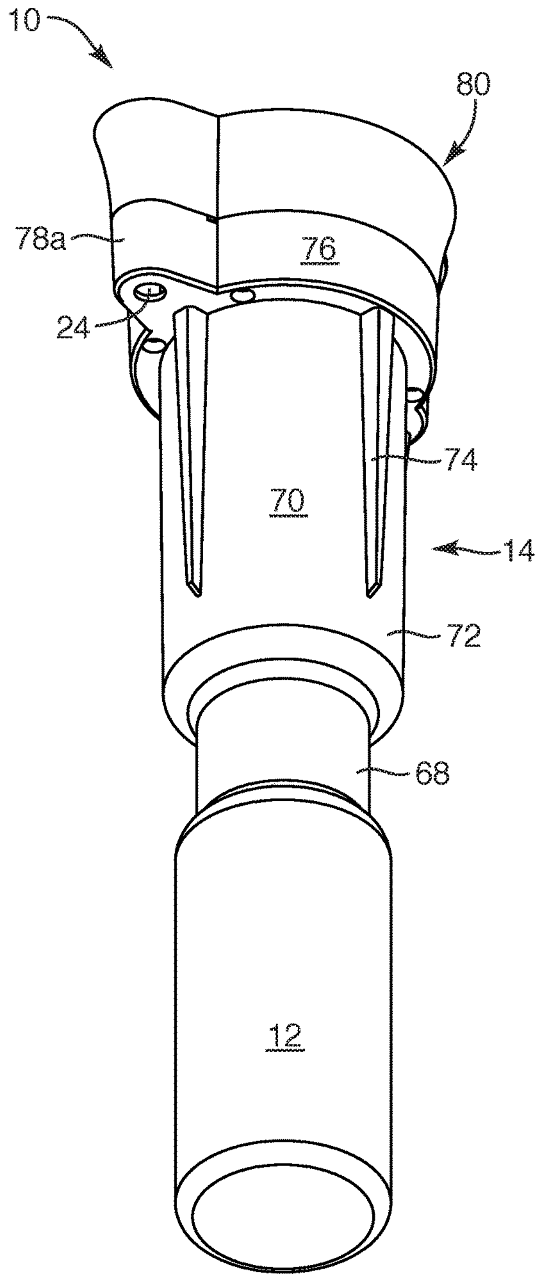
FIG. 7 is a lower quarter perspective view thereof from the air intake side thereof.
Figure 8:
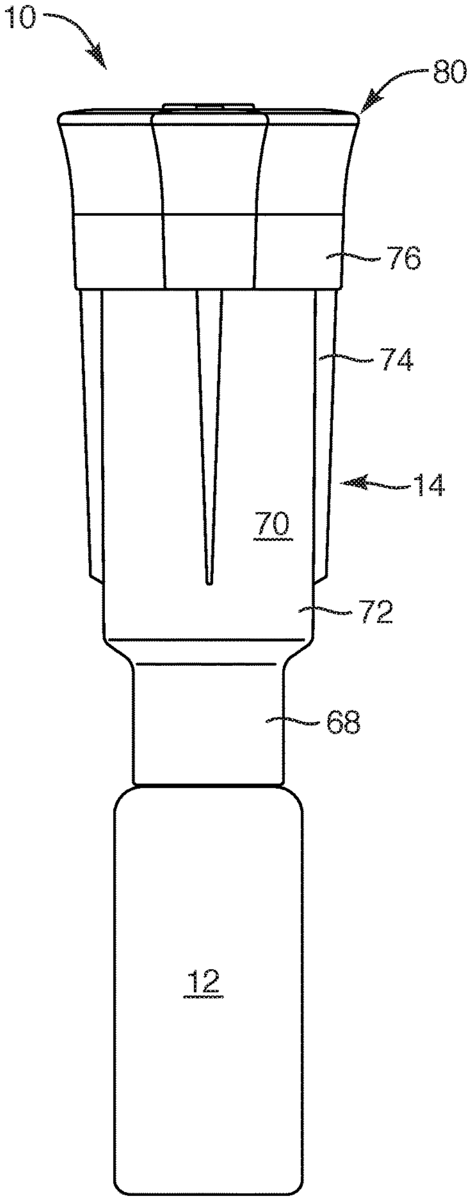
FIG. 8 is a front elevation view thereof.
Figure 9:
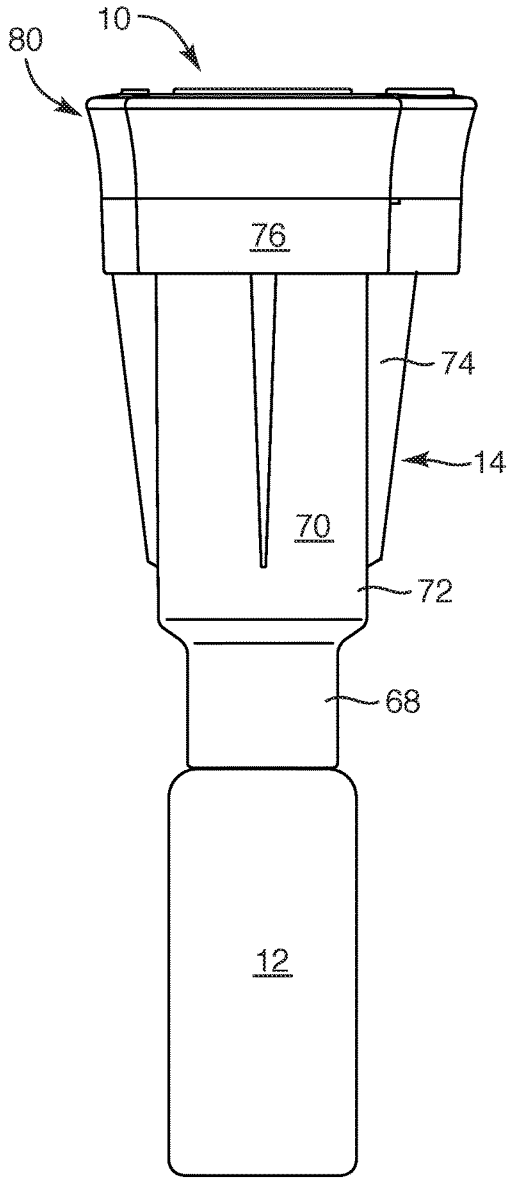
FIG. 9 is a right side elevation view thereof.
Figure 10:
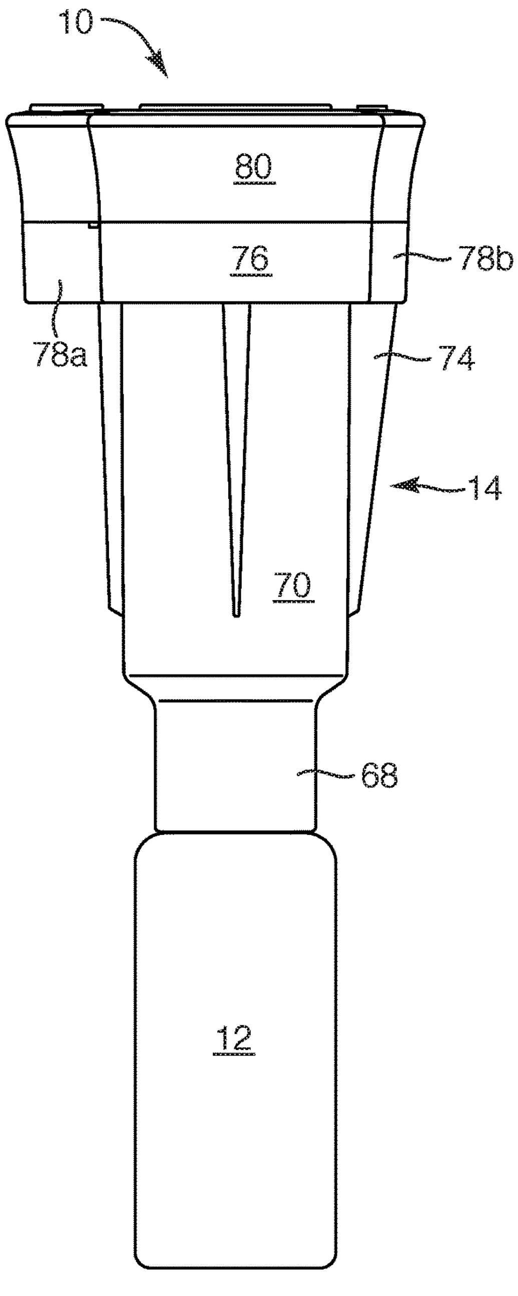
FIG. 10 is a left side elevation view thereof.
Figure 11:
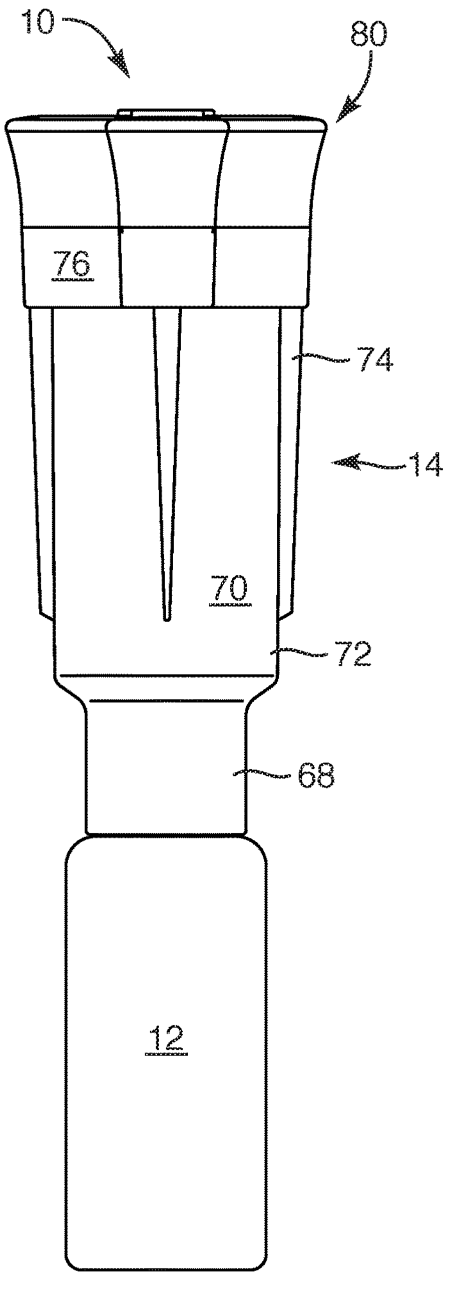
FIG. 11 is a rear elevation view thereof.
Figure 12:
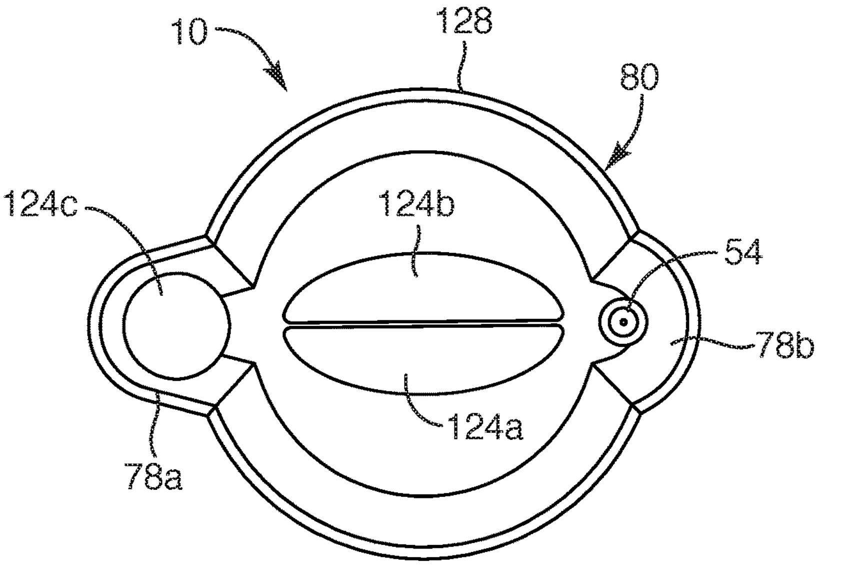
FIG. 12 is a top plan view thereof.
Figure 13:
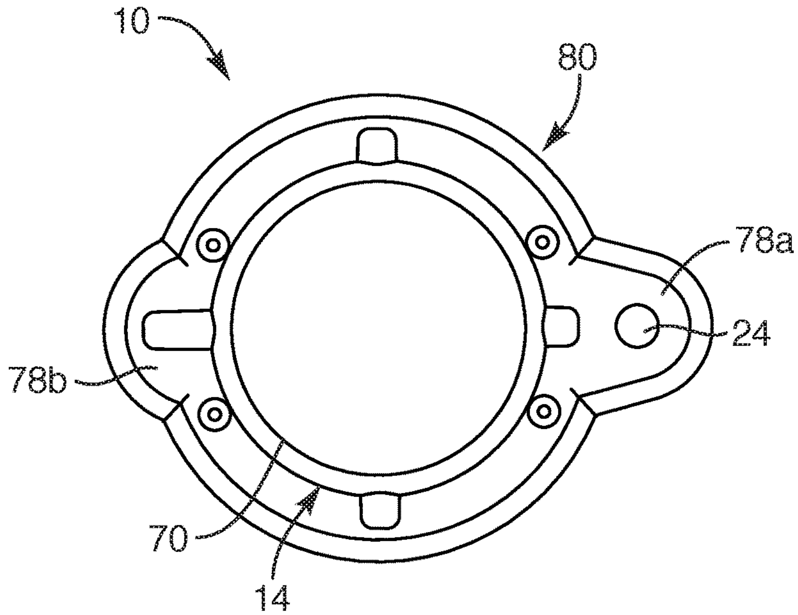
FIG. 13 is a bottom plan view thereof.

Referring to FIG. 3, but also specifically referring to FIGS. 1 through 3, and continuing to refer generally to FIGS. 1 through 29, the body 90 of the sleeve 16 has some features in common with the body 70 of the housing 14. For example, the body 90 of the sleeve 16 is provided with ears 91 or tabs 91. These tabs 91 or ears 91 act as anchors 91 to register and secure the body 90 into the collar 76 and body 70 of the housing 14. Specifically, the ears 91 are adapted to fit within the relief spaces 82 or sockets 82. Fasteners then pass through the tabs 91 to seat in the sockets 82 of the collar 76.

An adapter 92 operates as a receiver 92 for the siphon tube 58. Typically, an interference fit provides a fluid seal between the siphon tube 58 and the receiver 92, which acts as an adapter 92 into the eductor chamber 40. One may think of the eductor 20 as constituting a portion of the sleeve 16. For example, a sleeve 16 seals against the drive 18 by a seal 66*b* (see FIG. 2). That seal 66*b* connects the passage of air through the drive 18 and into the plenum 36.

The plenum 36, injecting through the nozzle 38 a jet of air, sends that jet of air into an eductor chamber 40. The eductor chamber 40, itself, is formed as in interior portion within a well 94 at the lower end of the sleeve 16. Thus, the drive 18 seals 66*b* against the well 94 of the sleeve 16. This seals the drive 18 also against any entry of the scented air flow passing from the drift chamber 44 into the annulus 50.

The well 94 effectively terminates the bottom end of the barrel 96 of the body 90 of the sleeve 16. Since the wall 98 of the barrel 96 operates as one wall 98 of the annulus 50, one can see that the wall 86 of the barrel 72 of the body 70 of the housing 14 forms the other wall 86 of the annulus 50.

All of this geometry simply shows the significance and benefit of the vertical integration of the essentially concentric drive 18, sleeve 16, housing 14, and reservoir 12. The result is such a compact structure that is not only self contained, but contains sealed passages and self cooling by the incoming air.

The effect of isolation by various seals 66 and the various walls 86, 98 of the system 10 provides additional sound proofing to render the system 10 more quiet, efficient, self cooling, and integrated into a smaller envelope than heretofore available. Here, envelope refers to the overall outer geometric volume, and its dimensions. Thus, here, the envelope is comparatively tall and comparatively narrow, with the system 10 comprised of effectively concentrically, vertically stacked components 12, 14, 16, 18, 20.

Just as the cap 80 fits the collar 76 to seal the body 70, forming a housing 14, the sleeve 16 has a cap 100. The cap 100 seals against the drive 18 by the seal 66*c*. The seal 66*d* effectively fits between the floor 104 of the cap 100 and an upper surface of the drive 18. Meanwhile, an outer wall 102 bounds or surrounds the cap 100, and fits the cap 100 inside the housing cap 80. Thus, the wall 102 of the drive cap 100 fits within the wall 87 of the housing cap 80.

In the illustrated embodiment, the cap 100 also includes an inlet lobe 106*a* and outlet lobe 106*b*. These lobes 106*a*, 106*b* serve to close off the inlet lobe 78*a* and outlet lobe 78*b* of the housing 14. However, a significant difference between the lobe 106*a* and the lobe 106*b* is that the lobe 106*b* contains a conduit 108 or chimney 108 that effectively contains the exit passage 44. That is, in some respect the conduit 108 is the exit passage 54. However, in another way of speaking, the exit passage 54 is the cavity or open space within the conduit 108 or chimney 108. Thus, one sees that a seal 66*e* about the conduit 108*a* seals the conduit 108 against the passage 109 in the collar 76 of the body 70 of the housing 14. Thus, the final drift chamber 52 is sealed in connection with the exit passage 54 by the seal 66*e* therebetween.

A controller 110 or control module 110 may be fabricated as, or on, a circuit board 110 with various components. In the illustrated embodiment, the control module 110 fits within the wall 102 or rim 102 of the drive cap 100. A cover portion 112 fits within the inlet lobe 106*a* to close off the inlet passage 26 or inlet chamber 26. In some embodiments, the inlet lobe 106*a* may also serve to seal off the inlet chamber 26.

However, in the illustrated embodiment, a perforation 30 through the floor 104 of the sleeve cap 100 serves to introduce a flow of inlet air entering through the inlet port 24 and inlet chamber 26 and passing into the plenum 32 by way of the perforation 30. Thus, the cover 112 or cover portion 112 of the control module 110 may tend to effect or create the chamber 32 or plenum 32.

Air passing through the chamber 32 will tend to cool the electronics 114 and other devices on the control module 110. For example, the electronics 114 may include circuit components, micro switches, wiring, and so forth. Typically, a recess 116 in the module 110 registers with and provides space for the conduit 108 to pass therethrough.

Various apertures 118 may be provided in various components in order to receive fasteners. Fasteners may thereby secure the various components 12, 14, 16, 18, 80, 100, 110 together.

In that regard, a control panel 120 may actually be provided with an aperture 122 supporting exit or passage of flows of air out from the exit passage 54. The aperture 122 may be sufficiently large to actually fit around the conduit 108, or may simply butt up against the conduit 108, thereby providing continuation of the exit passage 54 through the control panel 120. In order to fit, the lobes 126*a*, 126*b* may match the lobes 106*a*, 106*b* respectively in the cap 100.

A principal function of the control panel 120 is to provide buttons 124, such as, for example the buttons 124*a*, 124*b*, 124*c*. Herein, trailing letters behind reference numerals indicate specific instances of the item identified by the reference numeral. Accordingly, it is proper here to speak of a reference numeral alone, or a reference numeral with a trailing letter. The trailing letter indicates a specific instance. The reference numeral indicates all instances of the item. Thus, it is not necessary to cite every trailing reference letter, since a single mention of a reference numeral necessarily includes all of the specific instances identified in particular locations by the reference letters.

The buttons 124 may control various operational characteristics. For example, it has been found that users may be subjected to substantial trial and error in trying to adjust flow rates. For example, in other embodiments of apparatus and methods, controls have been implemented that control duty cycle, total time that the scented air may be injected into the atmosphere out of any overall period of time. For example, previous inventions by the instant inventor controlled the duration of systems in an “on” condition injecting scented air into the surrounding environment. Likewise, the overall time period was controlled. In other embodiments, the time “on” and the time “off” conditions together added to the total time for a single cycle. Thus, the fraction of time in the on condition can be controlled by controlling either the fraction of on time in the total cycle time or the comparative time as related to the delay time or comparative time off.

Here, in certain embodiments, the buttons 124 may control other parameters that are already integrated or have integrated the proportion of time on, the proportion of time off, the rate of flow, and the amount of introduced content 56 being entrained within the air flow.

Typically, the rim 128 on the cap 80 or housing cap 80 may provide a certain amount of protection, and rapid registration during installation. The control panel 120 will thus fit neatly, predictably, and stably onto the housing cap 80. A plate 129 may act as a wall 129 or cover 129. Meanwhile, seals 130 may be provided. The cavity 132 inside the cap 80 provides space for any of the electronics 114 on the control module 110 to be contained within the envelope of the cap 80.

Referring to FIGS. 4 through 13 and 20 through 29, the design and appearance of a system 10 in accordance with the invention may be comparatively tall and narrow. This provides many benefits, some functional, and some from a design point of view. Thus, the views embodied in these figures illustrate the design of one embodiment. The ribs 74 may be dispensed with by thickening the wall 86 of the body 70. Likewise, different materials may be formed of a foamed or expanded polymer rather than any solid molded polymer in forming the housing 14.

Referring to FIGS. 14 and 15, while continuing to refer generally to FIGS. 1 through 29, one may think of a passage 50 such as the annulus 50 between the sleeve 16 and the housing 14 as a conduit 50 carrying a fluid. The fluid is actually in two phases. One phase is vapor or gas such as air. The vapor may also include a certain amount of evaporated liquid content 56 from the reservoir 12.

In the illustrated embodiment, the flow 138 along the passage 50 is laminar. Accordingly, the flow 138 is distributed with a laminar velocity profile 140 or profile 140. The profile 140 reflects the variation in velocity 150 across a distance 146 measured from some origin 148, such as a wall, a center line, or the like along the passage 50.

In laminar flow 138, the flow 138 may be thought of as being represented by stream lines 142. The stream lines 142 effectively pass along a certain region of a passage 50. The velocity 150 measured at any distance 146 in the passage 50 is effectively the same. Thus, a centrally located stream line 142 indicates the maximum velocity in the passage 50. Meanwhile, velocity typically distributes along an effectively parabolic profile 140 eventually arriving at a zero value of velocity 150 at each wall 144.

In a system 10 in accordance with the invention, the overall distance 146 across the entire passage 50 is comparatively small compared to the length of the path in the direction of the velocity 150. For example, in a system in accordance with the system 10, the gap 50 or passage 50 is on the order of tens of thousandths of an inch. For example, a gap 50 of from about 50 to about 100 mils (thousandths) of an inch (e.g., a few millimeters) represents the total distance 146.

Meanwhile, the overall length along the path of the flow 138 may be a matter of multiple inches, for example, about two inches (five centimeters). An effect of the velocity profile 140 is that comparatively smaller droplets that are sufficiently small to effectively remain with the surrounding air, tend to operate or travel exactly as the vapor (air) in traveling along the passage 50.

By contrast, comparatively larger droplets are affected by faster air passing by them closer to the center or origin 148. Meanwhile, the velocity 150 is zero at the walls 144. Accordingly, larger droplets, of the second, heavier phase, generally, will be driven toward the outer walls 144. Thus, the closer to the origin 148 or the shorter the distance 146 from the origin 148, the faster the velocity 150 of flow 138. This results in the greater the tendency to carry only comparatively smaller droplets, the larger droplets having drifted out toward the wall 144.

At the wall 144, any impact of a liquid droplet will typically tend to cause coalescence or adherence to the wall 144. Some fracturing may create smaller particles. Thus, comparatively larger droplets move to the outside boundaries 144 of the passage 50, thus separating them out from the flow 138.

Referring to FIG. 15, one may think of the different regions 152 of the flow 138. In general, the velocity profile 140 illustrates how the velocity 150 actually varies across the channel 50 or passage 50. However, one may think of each of the sections 152 as a cylindrical core within a circular passage 50, or as a flat plate, effectively, in the annular passage 50 in accordance with the invention.

Closer to the center, the section 152*a* is traveling at the highest velocity 150. similarly, the section 152*b* is traveling at a lower velocity 150. Meanwhile, reduced velocity 140 in the section 152*c* ultimately leads to a zero velocity 150 at the wall 144, and its lowest velocity in the section 152*d.*

Thus, the various droplets 160 are subject to drifting 156 or drift 156 toward the walls 144. The comparatively larger droplets 160 will tend to lag the air flow and drift more laterally, toward the wall 144. The comparatively smaller droplets 160 will tend to entrain more completely with the surrounding air in the bulk flow 138.

It is important to understand that fluid drag exists between the bulk flow of air and the droplets 160. Meanwhile, momentum is mass multiplied by velocity. The velocity of the drift 156 is affected by the speed of the flow 138, or the velocity 150 of the bulk flow 138. However, because the momentum of a comparatively larger particle is greater (greater mass) than the momentum of a comparatively smaller particle, fluid drag must exert more force in order to provide the impulse. Impulse is force over (multiplied by) time which equates to a change in mass times velocity.

In the illustration, one may think of comparatively smaller droplets 160 as having motion which, if not Brownian, is at least so overwhelmed by the fluid drag on the individual particles 160, that those particles 160 move freely with the air. In contrast, the additional momentum and especially the relationship between surface area, or even cross-sectional area compared to overall mass and therefore momentum, has a dramatic effect (reduction) on the ability of fluid drag to change the direction of a larger particle 160.

Accordingly, comparatively larger particles 160 have a lower ratio of fluid drag force (proportional to cross-sectional area of the droplet 160 in the flow 138) compared to the momentum (mass times velocity, where mass is a function of diameter to the third power). Accordingly, as diameter of a droplet 160 goes up, mass goes up as a third power of diameter. Meanwhile, fluid drag only goes up as a square of diameter (cross-sectional area, in other words).

Referring to FIG. 16, in general, the flow 138 may be characterized by various dimensionless numbers, such as that of equation one. Here, N represents the Reynolds number. A Reynolds number represents a dimensionless number that relates the momentum forces to the frictional forces in a moving fluid. Thus, density and velocity as well as a significant length such as a dimension of a passage 50 control the numerator (upper) terms in the Reynolds number, while the viscosity is a denominator (lower) term. Again, this information is all available in standard engineering textbooks and other analyses.

Thus, density times velocity times a significant length, such as the entire effective diameter (typically distance 146 across the passage 50) represents the numerator. Viscosity represents the denominator. Meanwhile, all the units must be appropriate whether using an English system or the SI (international systems) of units.

Here, a Reynolds number is far below the threshold of about 2,000 (usually 2100). Again, 2,000 has no units, as it is a dimensionless number. In a system 10 in accordance with the invention, the Reynolds number is well into the laminar region, and does not even approach the value required for transition to turbulent flow.

In one illustrated embodiment, it has been found that a pump in the drive system 18 having a dead head pressure available of about thirteen psi (about one pascal) flows with about one quart per minute (0.9 liters per minute) of flow 138 when restricted only by the natural drag of the system 10. In one embodiment, a flow of about a pint per minute (0.45 liters per minute) flows at about a pressure of 0.7 pounds per square inch (0.05 pascal). In this instance, the orifice is about 0.015 inches (or about 0.5 millimeters).

Drag force, designated by F in FIG. 16, is equal to a combined group of constants referenced here by the letter K multiplied by the cross-sectional area of the object or droplet 160 on which the drag is acting, multiplied by the square of velocity. Velocity, represented here by the letter V, is the relative velocity between the droplet 160 and the surrounding fluid. Meanwhile, the drag force operating over a period of time is equal to the mass (M), multiplied by the change in velocity, V for a net change in momentum which is shown as the change (delta) in the overall momentum represented by MV.

Referring to FIG. 17, in a system 10 in accordance with the invention the system 10, itself may be installed, supported, ensconced, hidden, presented, or otherwise placed in, on, within, or in some other relationship with various cases, housings, or the like. For example, in the illustration, various means of positioning or locating the system 10 may be used. Thus, the system 10 is adaptable to virtually any décor, any design concept, or any environment. Whether in a floral arrangement, stand alone sculpture, or hidden within some other object, the system 10 need only receive electrical power to operate the drive system 18. Since the reservoir 12 and the entire eductor 20 exists within the system 10, no other constraints need be placed on the system 10 in order to operate.

In the illustrated examples, an air purifier 164*a* may include a system 10 in accordance with the invention. The system may be in close proximity to an intake port, outlet port, or simply nearby. In some embodiments, the system 10 may actually output its flow into the air stream passing through the air purifier, typically downstream of the purification process.

Likewise, a portable unit 164*b* may fit a cup holder in a vehicle, or be free-standing on a flat surface. For example, the unit 164*b* may include batteries or other power source to run the drive in the system 10.

Other shapes and devices such as a vase 164*d* or goblet 164*d* may be adapted to contain a system 10. Likewise, a floral arrangement 164*e* may ensconce the self-contained system 10. A clock radio **164*f* or other alarm clock 164*f* may include two systems 10**, one for a wake-up scent and one for a sleep-time scent.

Air conditioning units **164*g* may be easily adapted to include a system 10, in which only a small portion of the overall structure is visible. In fact, in some embodiments, it may be placed inside a vent. However, the illustrated embodiment is most easily accessed and controlled. Meanwhile, conventional dispensers 164*h* of disinfectants and the like, used as wall-mounted units 164*h* in many commercial establishments and public restrooms may also be adapted to receive a system 10** providing aromatic conditioning of the air.

Referring to FIGS. 18 and 19 and FIGS. 1 through 29 generally, some modifications to a system 10 in accordance with the invention in this embodiment may include, for example, locating the wall 98 of the sleeve 16 surrounding the drive 18 (pump and motor) eccentrically with respect to the body 70 of the housing 14. Accordingly, the gap between the wall 98 and the wall 86 is not uniform about the entire circumference. Also, a relief slot may be cut into the wall 86 to tune the performance as showing the wall 86 thickness on the right. This results in a larger effective diameter (hydraulic diameter) on one side of the passage 50 between the nozzle 42 and the final transit drift 52. On one side, the gap is smaller. The effective diameter, typically becomes the gap thickness when small gaps form the channel 50 or annulus 50. Thus, fluid drag is reduced in the passage 50 as the effective diameter (gap) and resulting Reynolds number increase.

In the illustrated embodiment, the seal **66*b* may be an O-ring, but is illustrated in this embodiment as a grommet providing additional filling and fitting for the interface between the nozzle 38, particularly near the plenum 36 and the barrel 96 of the sleeve 16 containing a drive 18** (motor and pump).

The top cap 80 that closes off the housing 14, still relies on buttons 124. However, those buttons 124 may pass through apertures 166 in a cover 168. The cover 168 is itself then covered by a panel 120. This panel 120 may be, effectively, a membrane 120. By touching the membrane 120, a user may actuate any of the switches 124, including a power button **124*a*, as well as the timer control buttons 124*b*, 124*c*. For example, the target 124*d* on the membrane 120 may depress the power button 124*a*** in response to finger pressure.

Indicator lights 164 suitably identified may shine through apertures 162 or windows 162 rendering the lights 164 visible through the membrane 120 or cover 120. In this embodiment, the button **124*a* is effectively a button 124*a* actuating inside the cap 80, under the touch location 124*d* that represents and contacts that button 124*a* under the membrane cover 120**.

Relief may be provided in order to permit the conduit 108 to pass therethrough on its way to exiting the system 10. Also, the stack up of components that form the cap 80 may be secured together by fasteners. The fasteners, such as screws, rivets, bolts, or the like may pass through individual components, such as through the apertures 178 into standoffs 176 for the purpose. Standoffs 176 provide for alignment of components by means of recesses 116 or relief 116 spaced apart and fitted to the various standoffs 176. Meanwhile, fasteners extending down through apertures 178 may be received into central hollows or apertures in the standoffs 176. Thus, the cap 80, once assembled with components fastened together may be handled as a single piece 80 or assembly 80.

In the illustrated embodiment, an apparatus 10 in accordance with the invention may be provided with a foam layer 172 effective to dampen sound and vibration originating from the drive 18. The foam layer 172 may be positioned between the drive 18 and the wall 98 of the sleeve 16.

In some embodiments, electrical plugs 170 may be provided to electronically connect the drive 18 to an outside source of power in a convenient manner. One or more plugs 170 may be provided in order to provide charging, power, control, or the like. In any basic embodiment, a single plug 170 may include multiple connections in order to carry one or more circuits of electricity as appropriate. In the illustrated embodiment, a controller 110 may be built upon a printed circuit board 110 on which electronic components 114 are interconnected to control timing, logic, switching as described above, and so forth as necessary.

The system 10 has been found to be somewhat more robust, particularly in view of the energy and dynamic nature of the drive 18, by provision of ribs 174 to add structural strength to the walls 98 of the sleeve 16 surrounding and supporting the drive 18, and supporting the eductor chamber 40. For example, the eductor 20 houses and supports the drive 18 by means of the grommet **66*b* or other seal 66*b*. Similarly, the grommet 66*b* or seal 66*b* forces the nozzle 38 down into the eductor chamber 40. Substantial force may be applied to the grommet 66*b*, in view of the effect of the cap 80 seating against resilient seals 66*c* applying force through the drive 18 to the well 94 and wall 98. The ribs 174 have been found effective to stiffen and strengthen the structure of the walls 98 of the sleeve 16 containing the drive 18, and strengthens the well 94** and securement thereto.

The annulus 50 may be tuned or trimmed. In this embodiment, the gap 50 may be about 0.050 to about 0.10 in inches across. Output is greatly reduced below about 0.030 inches. Separation degrades as the gap 50 increases over about 0.10 inches. The thickness of 0.060 inches in the wall 86 of the barrel 70 may be relieved by marking a channel therein of about 0.030 in depth and about 0.20 to about 0.35 width. A quarter inch of width tapering from a depth of zero at the bottom to about 0.030 inches at the top of the wall 86 (a height of about two to tow and a half inches) has been found effective to improve output with no loss in separation quality for oils deemed comparatively more viscous and more resinous, such as sandalwood and patchouli. Alternatively the entire gap 50 may be increased.

The present invention may be embodied in other specific forms without departing from its purposes, functions, structures, or operational characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A method of separating atomized droplets of a liquid, the method comprising: educting an essential oil from a reservoir into a flow of a stream of air; spraying the essential oil into a chamber as a distribution of droplets suspended in the flow; passing the distribution of droplets through a separator channel having an inner annulus wall and an outer annulus wall defining an aspect ratio of length-to-effective-diameter capable of drifting entrained droplets towards the inner annulus wall and the outer annulus wall during passage along a length; removing the entrained droplets from the distribution of droplets by lateral migration thereof across the flowto the inner and outer annulus walls; providing a material for the inner and outer annulus walls having a surface tension with the entrained droplets to create a force attracting the entrained droplets to the inner and outer annulus walls.

2. The method of claim 1, further comprising passing the flow vertically along the separator channel.

3. The method of claim 2, further comprising passing the flow upward along the separator channel.

4. The method of claim 1 further comprising coalescing the entrained droplets against the inner and outer annulus walls.

5. The method of claim 4, further comprising draining the entrained droplets toward the reservoir.

6. The method of claim 1, further comprising: providing a drive to pressurize the stream of air; providing the inner and outer annulus walls to be concentric with one another, and enclosing the drive; providing a first cooling channel between the drive and the inner and outer annulus walls; cooling the drive by drawing the stream of air into the drive by way of the first cooling channel; and thermally isolating the drive by passing the stream of air between the inner and outer annulus walls.

7. The method of claim 6, further comprising limiting transfer of sound from the drive by the first cooling channel and the separator channel.

8. The method of claim 7, further comprising controlling a duty cycle of the drive based on a size of space to be conditioned by the distribution of droplets and an intensity of conditioning of the size of space, both selected by a user and controlled by the duty cycle of the drive, where the duty cycle is represented by a relationship between a first time span in which the drive operates and a second time span selected from a total elapsed time and time spent by the drive not operating.

* * * * *